(12) United States Patent
Hayashi et al.

(10) Patent No.: US 12,369,785 B2
(45) Date of Patent: Jul. 29, 2025

(54) ENDOSCOPE SYSTEM WHICH DISPLAYS A CAPTURED IMAGE OF BIOLOGICAL TISSUE ON A SCREEN

(71) Applicant: HOYA CORPORATION, Tokyo (JP)

(72) Inventors: Yoshihiro Hayashi, Tokyo (JP); Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 765 days.

(21) Appl. No.: 17/768,742

(22) PCT Filed: Sep. 25, 2020

(86) PCT No.: PCT/JP2020/036430
§ 371 (c)(1),
(2) Date: Apr. 13, 2022

(87) PCT Pub. No.: WO2021/075235
PCT Pub. Date: Apr. 22, 2021

(65) Prior Publication Data
US 2023/0301491 A1    Sep. 28, 2023

(30) Foreign Application Priority Data
Oct. 18, 2019    (JP) ................................. 2019-190835

(51) Int. Cl.
*A61B 1/06* (2006.01)
*A61B 1/00* (2006.01)
(Continued)

(52) U.S. Cl.
CPC ........ *A61B 1/0655* (2022.02); *A61B 1/00009* (2013.01); *A61B 1/000095* (2022.02);
(Continued)

(58) Field of Classification Search
CPC .......... A61B 1/00009; A61B 1/000095; A61B 1/0661; H04N 23/6811; H04N 23/683;
(Continued)

(56) References Cited

U.S. PATENT DOCUMENTS 9,826,150 B2    11/2017  Naruse et al.
10,595,708 B2    3/2020  Kojima
(Continued)

FOREIGN PATENT DOCUMENTS

CN    105659582 A    6/2016
CN    107105982 A    8/2017
(Continued)

OTHER PUBLICATIONS

Office Action issued in Japanese Patent Application No. 2019-190835, dated Sep. 26, 2023, together with an English translation.
(Continued)

*Primary Examiner* — Anh Tuan T Nguyen
*Assistant Examiner* — Li-Ting Song
(74) *Attorney, Agent, or Firm* — GREENBLUM & BERNSTEIN, P.L.C.

(57) ABSTRACT

An endoscope system includes: a light source device; an electronic endoscope including an image sensor that images a biological tissue by a rolling shutter method; and a processor including an adjustment unit that is a part adjusting luminance of the frame image by combining adjustment of an exposure time of the image sensor with at least one of adjustment of light intensity of the illumination light and gain adjustment for determining a signal level of the frame image obtained from the image sensor, the adjustment unit determining whether or not a motion amount of an object image in the captured image or information regarding a blurring amount satisfies an adjustment condition and performing the adjustment processing by adjusting an adjust-
(Continued)

ment level representing a degree of strength of the adjustment processing by a magnitude of a value according to at least the determination result.

17 Claims, 21 Drawing Sheets

(51) Int. Cl.
| | |
|---|---|
| *A61B 1/045* | (2006.01) |
| *A61B 1/05* | (2006.01) |
| *G06T 7/00* | (2017.01) |
| *H04N 23/68* | (2023.01) |
| *H04N 23/72* | (2023.01) |
| *H04N 23/73* | (2023.01) |
| *H04N 23/74* | (2023.01) |
| *H04N 23/76* | (2023.01) |

(52) U.S. Cl.
CPC .......... *A61B 1/00045* (2013.01); *A61B 1/045* (2013.01); *A61B 1/05* (2013.01); *A61B 1/0661* (2013.01); *G06T 7/0012* (2013.01); *H04N 23/6811* (2023.01); *H04N 23/683* (2023.01); *H04N 23/72* (2023.01); *H04N 23/73* (2023.01); *H04N 23/74* (2023.01); *H04N 23/76* (2023.01); *G06T 2207/10068* (2013.01); *G06T 2207/30004* (2013.01); *G06T 2207/30168* (2013.01)

(58) Field of Classification Search
CPC ........ H04N 23/72; H04N 23/73; H04N 23/74; H04N 23/76; G06T 2207/30004; G06T 2207/10068
See application file for complete search history.

(56) References Cited

U.S. PATENT DOCUMENTS

| | | | | |
|---|---|---|---|---|
| 2011/0267520 | A1* | 11/2011 | Pyanet | ................... H04N 23/67 348/E5.091 |
| 2012/0071718 | A1 | 3/2012 | On | |
| 2014/0171737 | A1* | 6/2014 | Kagaya | ................. H04N 25/531 600/109 |
| 2015/0216460 | A1 | 8/2015 | Shigeta | |
| 2016/0360948 | A1* | 12/2016 | Mizuno | ................... A61B 1/051 |
| 2017/0135563 | A1 | 5/2017 | Uemori | |
| 2018/0227476 | A1 | 8/2018 | Kobayashi et al. | |
| 2019/0046022 | A1* | 2/2019 | Matsui | ................... G02B 23/26 |
| 2019/0142240 | A1 | 5/2019 | Hayashi | |
| 2019/0227288 | A1 | 7/2019 | Themelis | |
| 2019/0281221 | A1* | 9/2019 | Kuwahara | .............. H04N 5/265 |
| 2020/0234439 | A1* | 7/2020 | Chang | ................... G06T 7/0012 |

FOREIGN PATENT DOCUMENTS

| | | |
|---|---|---|
| EP | 1079255 B1 | 10/2008 |
| EP | 2743887 B1 | 3/2018 |
| JP | 2014-117412 A | 6/2014 |
| JP | 2014-117413 A | 6/2014 |
| JP | 2015-146924 A | 8/2015 |
| JP | 2016-87141 A | 5/2016 |
| JP | 2019-128353 A | 8/2019 |
| WO | 2017/065053 A1 | 4/2017 |
| WO | 2018/038269 A1 | 3/2018 |

OTHER PUBLICATIONS

International Search Report (ISR) dated Oct. 20, 2020 filed in PCT/JP2020/036430.
Office Action issued in European Patent Application No. 20876652.7, dated Oct. 11, 2023.
Office Action issued in European Patent Application No. 24163452.6, dated Nov. 15, 2024.
First Office Action issued in Chinese Patent Application No. 202080070685.0, dated Mar. 14, 2025, together with an English translation.

* cited by examiner

FIG. 15
(a) 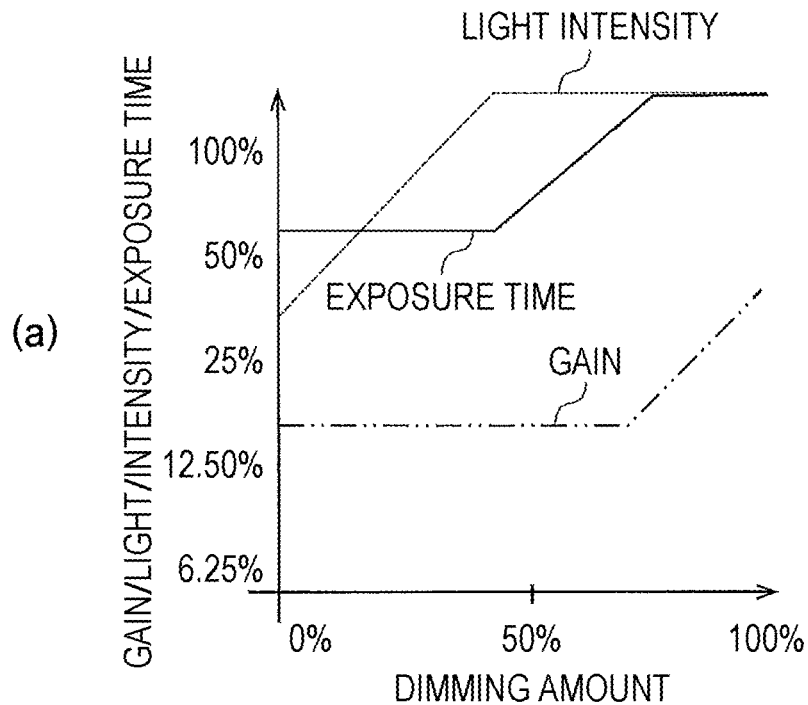
(b) 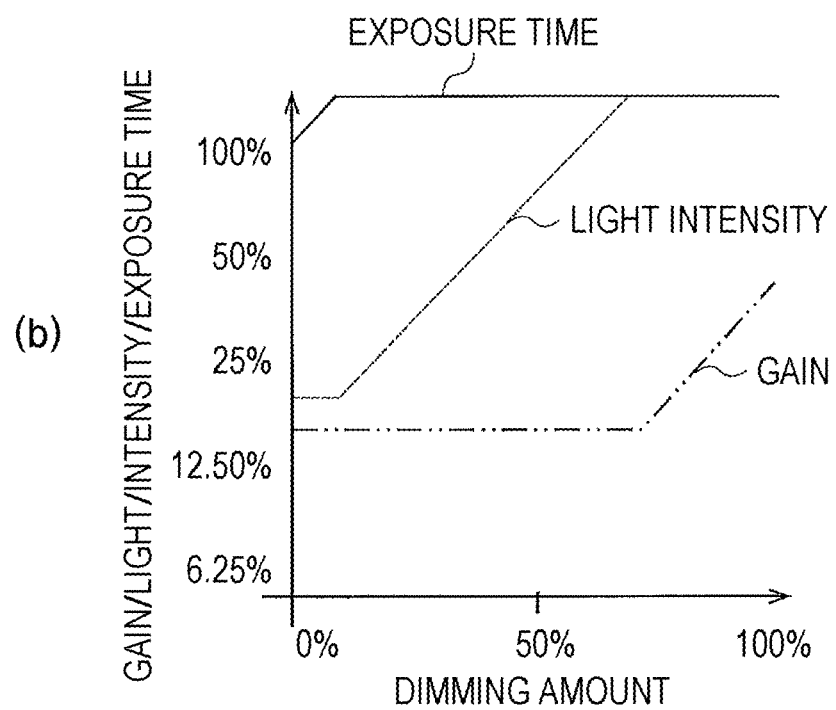

ENDOSCOPE SYSTEM WHICH DISPLAYS A CAPTURED IMAGE OF BIOLOGICAL TISSUE ON A SCREEN

TECHNICAL FIELD

The present invention relates to an endoscope system that displays, on a screen, a captured image of a biological tissue in a body cavity.

BACKGROUND ART

An endoscope system includes: an electronic endoscope including an image sensor that images a biological tissue; a processor including an image processing unit configured to process an image of the imaged biological tissue to create a display image; and a monitor connected to the processor and configured to display the created display image.

In recent years, a CMOS image sensor is often used as an image sensor used for the electronic endoscope. In the case of using the CMOS image sensor, a rolling shutter method is used as an exposure/output method for exposing a light receiving surface of the CMOS image sensor and outputting an image.

The rolling shutter method is a method of dividing the light receiving surface of the image sensor into a plurality of regions for each scanning line and performing exposure sequentially with time intervals for each region, in which accumulated electric charges are sequentially reset for each region, and then accumulation of the electric charges by exposure is started and the accumulated electric charges to be an image signal are output (read).

In a case where such a rolling shutter image sensor is used, since the motion of the biological tissue as an object is slow, even when an object image is exposed sequentially with time intervals, there are few cases where the object image is shifted at the boundary of the scanning line. However, in a case where a liquid droplet flies around the biological tissue at a high speed and a liquid adheres to a surface of an observation window provided on a front surface of the image sensor to form a liquid flow, a moving speed of the liquid droplet or the liquid flow is faster than a motion of the biological tissue, and thus, in a portion corresponding to the boundary of the scanning line in a frame image, an image of the liquid droplet or an image of the biological tissue viewed through the liquid flow is often shifted along a line corresponding to the scanning line. That is, due to the rolling shutter method, an artifact often occurs along the line corresponding to the scanning line of the image sensor in the frame image.

With respect to the problem of the image of the liquid droplet at the time of the flying of the liquid droplet, there is known an endoscope apparatus that prevents an observer from visually recognizing an edging phenomenon in which an unnatural edge occurs in a liquid droplet image reflected on an observation image of the endoscope (Patent Literatures 1 and 2).

In the endoscope apparatus, it is determined whether or not the edging phenomenon in which an edge in a horizontal direction occurs in a scattered liquid droplet image occurs in the frame image captured by a CMOS image sensor, and in a case where the edging phenomenon occurs, the edging phenomenon reducing processing is performed to reduce the edging phenomenon.

As the edging phenomenon reducing processing, the edging phenomenon is reduced by increasing an exposure time or performing blurring processing.

CITATION LIST

Patent Literature

Patent Literature 1: JP 2014-117413 A
Patent Literature 2: JP 2014-117412 A

SUMMARY OF INVENTION

Technical Problem

In the above-described endoscope apparatus, since the edging phenomenon reducing processing is performed after it is determined that the edging phenomenon occurs, the edging phenomenon always occurs on a display screen of a monitor. A screen display of the edging phenomenon is a noise component for an operator who operates the endoscope, and may cause erroneous determination for the biological tissue.

Furthermore, in the above-described endoscope apparatus, in a case where the edging phenomenon occurs, when the exposure time is increased as the edging phenomenon reducing processing, a problem that the image becomes excessively bright and the operator feels discomfort occurs. Therefore, it is necessary to adjust the exposure time without changing the brightness of the screen, but the above-described endoscope apparatus does not cope with the above-described problem.

Furthermore, in the above-described endoscope apparatus, in a case where the edging phenomenon occurs, when the blurring processing is performed only on the edge portion as the edging phenomenon reducing processing, the image becomes an unnatural image, and when the blurring processing is performed on the entire screen, a region desired to be observed also becomes a blurred image, which gives discomfort to the operator.

Therefore, an object of the present invention is to provide an endoscope system capable of performing adjustment processing including an adjustment level, which is processing for suppressing occurrence of the artifact along a line corresponding to the scanning line of the image sensor in the frame image when the biological tissue is imaged as a moving image by the rolling shutter method, without significantly changing a luminance level of the image.

Solution to Problem

An aspect of the present invention is an endoscope system that displays, on a screen, a captured image of a biological tissue in a body cavity. The endoscope system includes:
  a light source device configured to generate illumination light illuminating the biological tissue;
  an electronic endoscope including an image sensor configured to capture the biological tissue as a moving image by a rolling shutter method;
  a processor including an image processing unit configured to perform image processing on a frame image obtained by image capturing of the image sensor, and an adjustment unit that is a part performing adjustment processing of adjusting luminance of the frame image by combining adjustment of an exposure time of the image sensor with at least one of adjustment of light intensity of the illumination light and gain adjustment for determining a signal level of an imaging signal of the frame image obtained from the image sensor, the adjustment unit being configured to perform adjustment determination including determination of whether or not at least one of first information regarding a motion amount between adjacent frame images of an object image in the captured image or second information regarding a blurring amount of an edge of the object image in the captured image satisfies an adjustment condition, and perform the adjustment processing by adjusting an adjustment level representing a degree of strength of the adjustment processing by a magnitude of a value according to a determination result of the adjustment determination; and, a monitor configured to display the frame image subjected to the image processing on the screen.

It is preferable that the first information regarding the motion amount includes at least one of the motion amount of the object image in a current frame image or a change amount in the motion amount of the object image in the current frame image with respect to the motion amount of the object image in an immediately previous frame image.

It is preferable that the second information regarding the blurring amount includes at least one of a blurring amount of the object image in the current frame image or a change amount in the blurring amount of the object image in the current frame image with respect to the blurring amount of the object image in the immediately previous frame image.

It is preferable that the adjustment unit adjusts a luminance level of an image obtained by the image sensor by using a dimming amount set to decrease a value from a currently set value in a case where the luminance level of a current frame image is greater than a target luminance level and increase a value from the currently set value in a case where the luminance level of the current frame image is less than the target luminance level, the dimming amount being a parameter for performing adjustment such that the luminance level of the current frame image acquired by the image capturing of the image sensor is the target luminance level.

It is preferable that the adjustment unit further determines whether or not third information regarding the dimming amount satisfies the adjustment condition as the adjustment determination, and the determination result of the adjustment determination includes a determination result for the third information.

It is preferable that the third information regarding the dimming amount includes at least one of a change amount in the current dimming amount with respect to the immediately previous dimming amount or a maintaining time for maintaining the dimming amount at a value lower than a predetermined value.

It is preferable that the frame image includes a display region in which the object image is displayed, and a vignetting region in which luminance is lower than that of the display region due to an imaging optical system of the electronic endoscope, the object image is not displayed, the vignetting region being formed outside the display region, the adjustment unit further determines whether or not fourth information regarding a pixel value in the vignetting region satisfies the adjustment condition, and the adjustment unit is configured to adjust the adjustment level according to the determination result for the fourth information.

It is preferable that the fourth information regarding a pixel value of the vignetting region includes at least one of an integrated value of pixel values in the vignetting region, the number of pixels of which the pixel value in the vignetting region exceeds a predetermined threshold, a change amount in the integrated value obtained from the frame image immediately before a current frame image, or a change amount in the number of pixels obtained from the frame image immediately before the current frame image.

It is preferable that the adjustment unit performs the adjustment determination every time the frame image is obtained from the image sensor, and in a case where the adjustment determination result is affirmative, the adjustment unit makes a value of the adjustment level greater than a value of the adjustment level determined in an immediately previous frame image.

At this time, it is preferable that the adjustment unit performs a plurality of determinations as the adjustment determination, and in a case where the determination result of at least one determination or at least two determinations among a plurality of the determinations is affirmative, the determination result of the adjustment determination is affirmative.

It is preferable that in a case where the determination result of the adjustment determination by the adjustment unit is negative and the integrated value of the pixel values in the vignetting region or the number of the pixels is greater than a predetermined threshold, a value of the adjustment level is maintained at a value of the adjustment level determined in the immediately previous frame image.

It is preferable that in a case where the determination result of the adjustment determination by the adjustment unit is negative and the integrated value of the pixel values in the vignetting region or the number of the pixels is equal to or less than the predetermined threshold, a value of the adjustment level in the current frame image is made smaller than a value of the adjustment level determined in the immediately previous frame image.

It is preferable that the adjustment unit includes an index calculation unit that calculates an index indicating a degree of an occurrence amount of an artifact that occurs along a line corresponding to a scanning line of the image sensor due to the rolling shutter method in the frame image, and in a case where the determination result of the adjustment determination by the adjustment unit is negative and the index is greater than a predetermined threshold, a value of the adjustment level is maintained at a value of the adjustment level determined in an immediately previous frame image.

It is preferable that in a case where the determination result of the adjustment determination by the adjustment unit is negative and the index is equal to or less than a predetermined threshold, a value of the adjustment level in the current frame image is made smaller than a value of the adjustment level determined in the immediately previous frame image.

Another aspect of the present invention is an endoscope system that displays, on a screen, an image obtained by capturing a biological tissue in a body cavity. The endoscope system includes:

a light source device configured to generate illumination light illuminating the biological tissue;

an electronic endoscope including an image sensor configured to capture the biological tissue as a moving image by a rolling shutter method;

a processor including an image processing unit configured to perform image processing on a frame image obtained by image capturing of the image sensor, an index calculation unit configured to calculate an artifact occurrence index indicating a degree that an artifact occurs along a line corresponding to a scanning line of the image sensor in the frame image due to the rolling shutter method, and an adjustment unit that is a part performing adjustment processing of adjusting luminance of the frame image by combining adjustment of an exposure time of the image sensor with at least one of adjustment of light intensity of the illumination light or gain adjustment for determining a signal level of an imaging signal of the frame image obtained from the image sensor, the adjustment unit being configured to perform the adjustment processing by adjusting an adjustment level representing a degree of strength of the adjustment processing by a magnitude of a value according to a determination result of whether or not the magnitude of the artifact occurrence index satisfies an adjustment condition; and, a monitor configured to display the frame image subjected to the image processing on the screen.

It is preferable that the adjustment unit adjusts a luminance level of an image obtained by the image sensor by using a dimming amount set to decrease a value from a currently set value in a case where the luminance level of a current frame image is greater than a target luminance level and increase a value from the currently set value in a case where the luminance level of the current frame image is less than the target luminance level, the dimming amount being a parameter for performing adjustment such that the luminance level of the current frame image acquired by the image capturing of the image sensor is the target luminance level.

It is preferable that the adjustment unit includes a first reference table and a second reference table which determine a level of the light intensity, a time length of the exposure time, and a gain level of the gain adjustment with respect to the dimming amount, the products obtained by multiplying each value of the level of the light intensity, the time length of the exposure time, and the gain level of the gain adjustment with respect to the value of the dimming amount coincide with each other between the first reference table and the second reference table over an entire range of possible values of the dimming amount, and a correspondence relationship of the level of the light intensity with respect to the value of the dimming amount and a correspondence relationship of the time length of the exposure time with respect to the value of the dimming amount are different from each other between the first reference table and the second reference table, and by using a first set value of each of the level of the light intensity, the time length of the exposure time, and the gain level, which are determined from the first reference table according to the value of the dimming amount, and a second set value of each of the level of the light intensity, the time length of the exposure time, and the gain level, which are determined from the second reference table according to the value of the dimming amount, the adjustment unit is configured to determine an adjustment value of the level of the light intensity, the adjustment value of the time length of the exposure time, and the adjustment value of the gain level which are used in the adjustment processing by performing interpolation according to the adjustment level between the first set value and the second set value corresponding to the first set value.

Furthermore, it is preferable that in both of the first reference table and the second reference table, the product obtained by multiplying each value of the level of the light intensity, the time length of the exposure time, and the gain level at a maximum value of the dimming amount is greater than the product obtained by multiplying each value of the level of the light intensity, the time length of the exposure time, and the gain level at a minimum value of the dimming amount, the time length of the exposure time of the second reference table is not shorter than the time length of the corresponding exposure time of the first reference table over the entire range of the possible values of the dimming amount, and the product of the value of the level of the light intensity and the value of the gain level in the second reference table is not greater than the product of the value of the level of the corresponding light intensity and the value of the corresponding gain level in the first reference table over the entire range of the possible values of the dimming amount.

It is preferable that the first reference table and the second reference table have a range of the dimming amount in which with respect to the value of the dimming amount, the time length of the exposure time of the second reference table is longer than the time length of the exposure time of the first reference table, and the level of the light intensity of the second reference table is smaller than the level of the light intensity of the first reference table.

It is preferable that a value of the adjustment level is higher as a degree of the adjustment processing is stronger, and the adjustment value approaches the second set value as the value of the adjustment level is higher.

Advantageous Effects of Invention

According to the endoscope system described above, adjustment processing including an adjustment level, which is processing of suppressing occurrence of the artifact along a line corresponding to the scanning line of the image sensor in the frame image when the biological tissue is imaged as a moving image by the rolling shutter method, can be performed without significantly changing a luminance level of the image.

BRIEF DESCRIPTION OF DRAWINGS

FIG. 15(a) is a diagram illustrating an example of a normal reference table used in an endoscope system according to an embodiment, and FIG. 15(b) is a diagram illustrating an example of an RSA reduction reference table used in the endoscope system according to the embodiment.

DESCRIPTION OF EMBODIMENTS

Hereinafter, an endoscope system according to an embodiment will be described with reference to the drawings.

Figure 1:
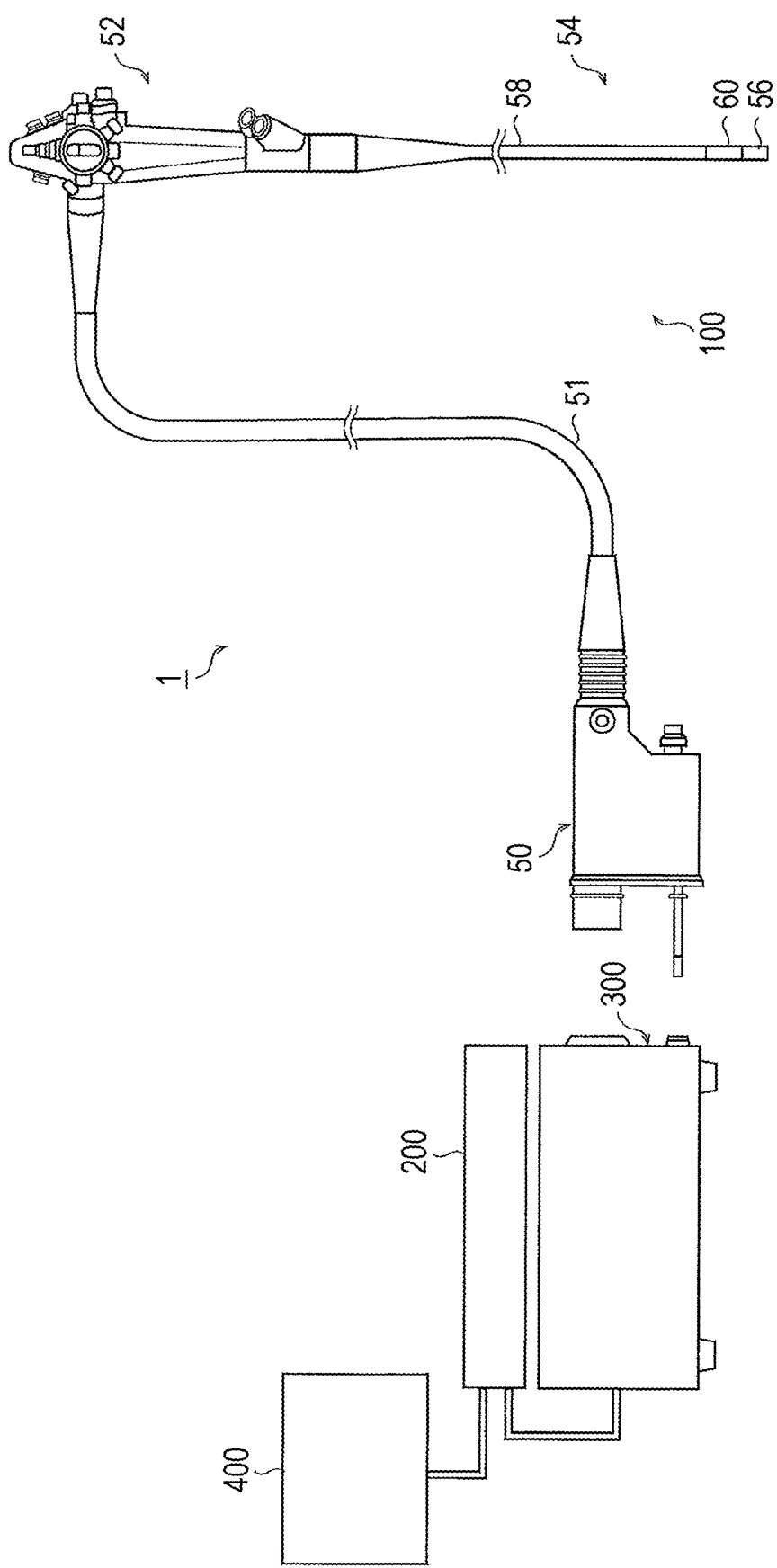
FIG. 1 is an external perspective view of an endoscope system according to an embodiment.
Figure 2:
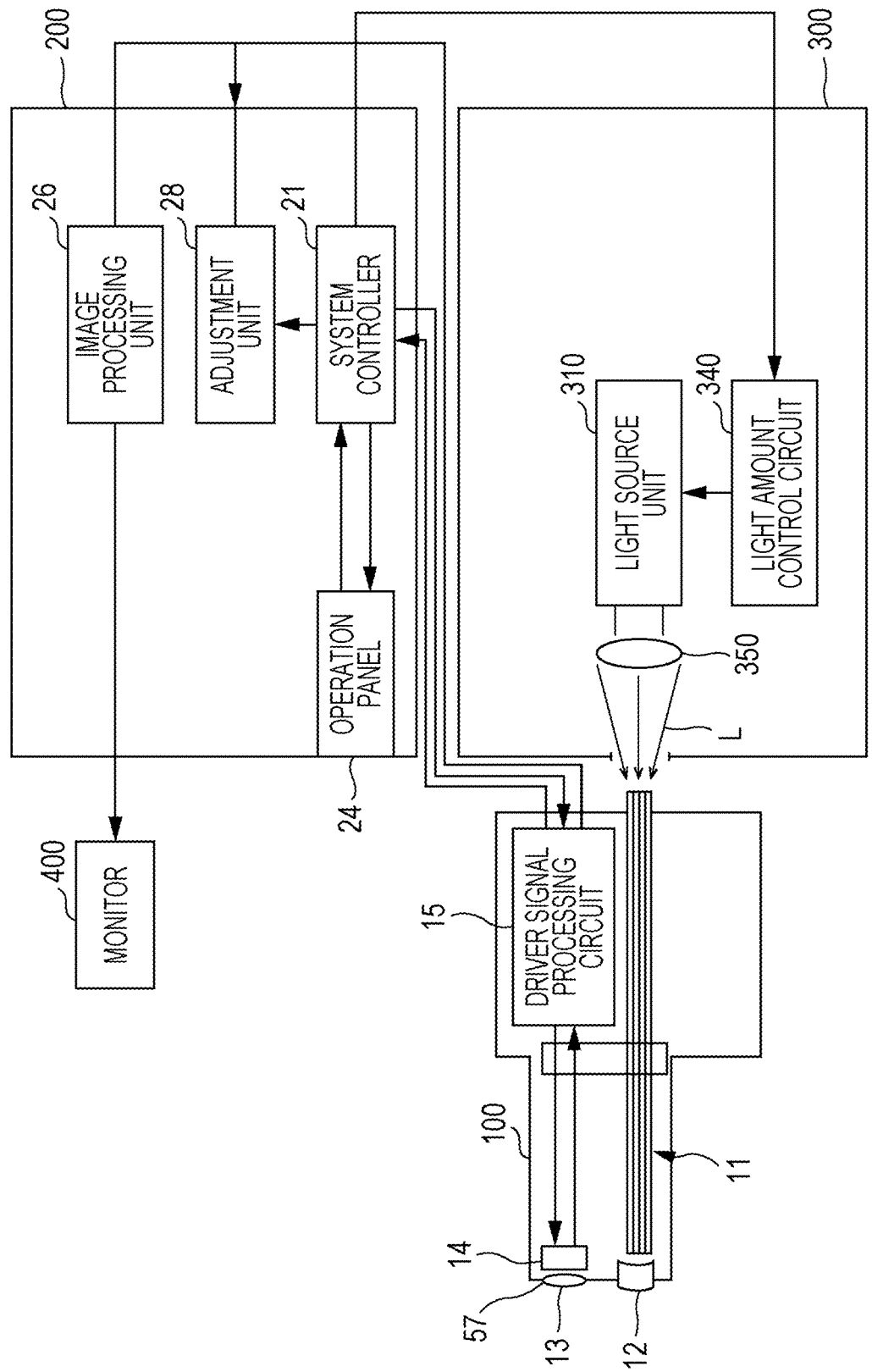
FIG. 2 is a block diagram illustrating a configuration of an endoscope system according to an embodiment.
Figure 3:
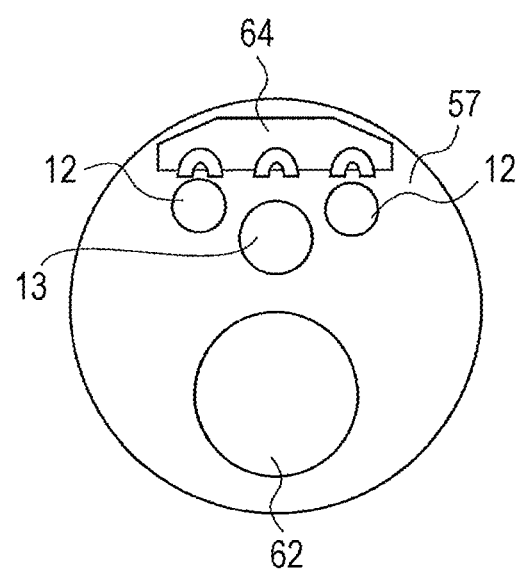
FIG. 3 is a view illustrating an example of a distal end surface of a distal tip of an endoscope according to an embodiment.

FIG. 1 is an external perspective view of an endoscope system 1 according to the embodiment, and FIG. 2 is a block diagram illustrating a configuration of the endoscope system according to the embodiment. FIG. 3 is a view illustrating an example of a distal end surface of a distal tip of an endoscope according to the embodiment.

The electronic endoscope system 1 illustrated in FIG. 1 is a system specialized for medical use, and includes an electronic endoscope (hereinafter, electronic scope) 100, a processor 200, a light source device 300, and a monitor 400. The electronic scope 100, the light source device 300, and the monitor 400 are each connected to the processor 200.

Note that although the light source device 300 and the processor 200 are configured separately, the light source device 300 may be integrally provided in the processor 200.

As illustrated in FIG. 2, the processor 200 includes a system controller 21. The system controller 21 is control means for executing various programs stored in a memory (not illustrated) and integrally controlling the entire endoscope system 1, and is configured by software or hardware. Furthermore, the system controller 21 is connected to an operation panel 24. The system controller 21 changes each operation of the endoscope system 1 and a parameter for each operation in accordance with an operator's instruction input to the operation panel 24. The operator's input instruction includes, for example, an instruction to switch an observation mode of the electronic endoscope system 1. The observation mode includes a normal observation mode in which white light is observed as illumination light, and a special observation mode in which special light is observed as illumination light.

Moreover, the processor 200 includes an image processing unit 26 and an adjustment unit 28.

The image processing unit 26 is configured to perform image processing on a frame image obtained by imaging by using the image sensor of the electronic scope 100.

The adjustment unit 28 is configured to perform adjustment processing of adjusting the luminance of the frame image by combining adjustment of the exposure time of the image sensor with at least one of adjustment of the light intensity of the illumination light and gain adjustment for determining a signal level of an imaging signal of the frame image obtained from the image sensor. Details will be described later.

Furthermore, although not illustrated, the processor 200 includes a timing controller. The timing controller outputs a clock pulse for adjusting an operation timing of each unit to each circuit in the endoscope system 1.

The light source device 300 includes a light source unit 310, a light amount control circuit 340, and a condenser lens 350. In accordance with an instruction from the system controller 21, the light amount control circuit 340 generates a drive signal for changing a level of the light intensity of a light source, and outputs the drive signal to the light source unit 310. The light source unit 310 emits light at a set light intensity level as illumination light for illuminating the biological tissue. The light includes at least white light, and may include special light in a specific wavelength band. The light source unit 310 includes a xenon lamp that emits white light, an LED that emits special light, a laser diode, and the like. Furthermore, the special light may be generated by transmitting the white light through an optical filter.

As illustrated in FIG. 2, illumination light L emitted from the light source unit 310 is focused by the condenser lens 350 onto an incident end face of a Light Carrying Bundle (LCB) 11 to be described, which is configured by a bundle of a plurality of optical fibers, to be incident into the LCB 11.

As illustrated in FIG. 1, the electronic scope 100 mainly includes a connection unit 50, an operation unit 52, an insertion portion 54, and a cable 51 that connects the connection unit 50 with the operation unit 52. The insertion portion 54 includes a flexible tube 58 that connects the operation unit 52 and a distal tip 56 of the insertion portion 54. The flexible tube 58 is provided with the LCB 11, an air/water supply tube for sending fluid such as water or air, a treatment tool introduction tube, a signal line, and the like. The treatment tool introduction tube is a tube through which a treatment tool for treating (for example, cutting and removing) a biological tissue is caused to protrude from the distal tip 56 by the operation unit 52, the treatment tool being caused to pass through the tube in order to treat the biological tissue by the operation unit 52. The signal line includes a transmission line for transmitting a captured image signal from an image sensor 14 to be described later and a control line for transmitting a control signal from the processor 200 to the image sensor 14.

The distal tip of the electronic scope 100 is the insertion portion 54 having flexibility for insertion into a human body. A bending portion 60 connected to a base end of the insertion portion 54 is provided in the vicinity of the distal tip of the insertion portion 54, and the bending portion 60 is bent according to a remote operation with the operation unit 52. A bending mechanism of the bending portion 60 is a known mechanism incorporated in a general endoscope. In the bending structure, the bending portion 60 is bent by pulling an operation wire in conjunction with a rotation operation of a bending operation knob provided in the operation unit 52. The distal tip 56 including the image sensor 14 is provided at a distal tip of the bending portion 60.

At the distal tip 56 of the electronic scope 100, there is an illumination light emitting end of the LCB 11 disposed over substantially the entire length from the connection unit 50 to the distal tip 56.

As illustrated in FIG. 2, at the distal tip 56, a light distribution lens is provided in the front of the illumination light emitting end of the LCB 11, and a front surface of the light distribution lens on the biological tissue side is an illumination window 12 that emits illumination light. Furthermore, an objective lens that forms an image of the biological tissue is provided at the distal tip 56, and the front surface of the objective lens on the biological tissue side is an observation window 13 that receives light of the image of the biological tissue. Moreover, the image sensor 14 that receives the formed image, an amplifier (not illustrated) that amplifies an image signal output from the image sensor 14 are provided at the distal tip 56.

The illumination light incident into the LCB 11 propagates in the LCB 11, is emitted from the illumination light emitting end of the LCB 11, and illuminates the object of the biological tissue as the illumination light L through the illumination window 12 including the light distribution lens. Return light of the illumination light L emitted from the illumination window 12, the return light being from the object, forms an optical image on a light receiving surface of the image sensor 14 via the observation window 13 configured by the objective lens.

Note that in a case where the light source unit 310 of the light source device 300 has a compact configuration, the light source unit 310 may be incorporated in the distal tip 56 of the electronic scope 100. In this case, the LCB 11 that guides the illumination light L from the light source unit 310 to the distal tip 56 and the condenser lens 350 are unnecessary.

FIG. 3 illustrates an example of a distal end surface 57 of the distal tip 56. On the distal end surface 57, two illumination windows 12 configured by the light distribution lens provided in front of the distal tip of the LCB 11 are provided, and moreover, the observation window 13 configured by the objective lens is provided so as to be sandwiched between the illumination windows 12. Furthermore, the distal end surface 57 includes a treatment tool opening 62 through which a treatment tool protrudes from the distal end surface 57, and an air/water supply port 64 (fluid ejection port) through which a fluid for cleaning the illumination window 12 and the observation window 13 is ejected. The air/water supply port 64 is, for example, a portion that receives supply of fluid from a fluid delivery mechanism (not illustrated) connected to the operation unit 52 via an air/water supply tube in the flexible tube 58 and ejects the fluid. Specifically, the air/water supply port 64 includes three ejection nozzles, and the ejection nozzles are configured to blow water and air to each of two illumination windows 12 and one observation window 13 to clean.

Furthermore, instead of the distal end surface 57 illustrated in FIG. 3, the air/water supply port 64 may be provided with an air supply port for ejecting air and a water supply port for ejecting water separately.

The image sensor 14 is a color image sensor having a predetermined pixel arrangement, for example, a complementary metal oxide semiconductor (CMOS) image sensor. The image sensor 14 accumulates an optical image formed by each of pixels on the light receiving surface, as electric charges corresponding to a light amount, and generates and outputs image signals of Red (R), Green (G), and Blue (B). A color filter for determining a sensitivity wavelength band in an image color component of a captured image of the image sensor 14 is provided in front of each light receiving position of the image sensor 14. As the color filter, for example, primary color filters of red (R), green (G), and blue (B) are used. The image sensor 14 repeatedly images the biological tissue at timing according to the clock pulse transmitted from the processor 200.

Note that the image sensor 14 captures an image by the rolling shutter method. Specifically, in the image capturing by the rolling shutter method is a method of setting one line or a plurality of lines of pixels extending in the lateral direction of the light receiving surface of the image sensor 14 as one pixel region and performing exposure for each pixel region sequentially with time intervals, in which accumulated electric charges are sequentially reset for each pixel region, and then accumulation of the electric charges by exposure is started and the accumulated electric charges to be an image signal are output (read). Therefore, in one captured frame image, the exposure timing is shifted at regular time intervals for each line or for each of a plurality of lines.

As illustrated in FIG. 2, a driver signal processing circuit 15 and a memory (not illustrated) are provided in the connection unit 50 of the electronic scope 100. An image signal of the biological tissue is input to the driver signal processing circuit 15 from the image sensor 14 at a frame cycle. The frame cycle is, for example, 1/30 seconds. The driver signal processing circuit 15 performs predetermined processing on the image signal sent from the image sensor 14 and outputs the processed image signal to the image processing unit 26 and the adjustment unit 28 of the processor 200.

The driver signal processing circuit 15 also accesses the memory (not illustrated) and reads specific information of the electronic scope 100. For example, the specific information of the electronic scope 100 recorded in the memory includes the number of pixels or sensitivity of the image sensor 14, a frame rate with which the electronic scope 100 is operable, and a model number. The driver signal processing circuit 15 outputs the specific information read from the memory to the system controller 21.

The system controller 21 performs various calculations based on the specific information of the electronic scope 100 and generates a control signal. The timing controller (not illustrated) controls the operation and timing of each unit of the endoscope system 1 so as to perform processing suitable for the electronic scope 100 connected to the processor 200 by using the generated control signal.

The driver signal processing circuit 15 receives supply of a clock pulse from the timing controller (not illustrated) in accordance with timing control by the system controller 21. The driver signal processing circuit 15 performs driving control of the image sensor 14 at timing synchronized with the frame rate of the image processed on the processor 200 side in accordance with the supplied clock pulse. According to this, the image sensor 14 continuously images the object to continuously generate the image signal of the frame image of the object.

The image processing unit 26 performs predetermined image processing such as demosaic processing, matrix calculation, and color balance processing on the image signal of the captured image, which is input at one frame cycle, from the driver signal processing circuit 15 and outputs the processed image signal to a frame memory (not illustrated). The frame memory buffers the input image signal and outputs the image signal according to predetermined timing control. Moreover, the image processing unit 26 processes the output image signal to generate monitor display screen data, and converts the generated monitor display screen data into a predetermined video format signal. The converted video format signal is output to the monitor 400. According to this, the moving image of the biological tissue imaged by the electronic scope 100 is displayed on the display screen of the monitor 400. That is, the monitor 400 is configured to display the frame image subjected to the image processing on the screen.

The adjustment unit 28 is a part that performs adjustment processing of adjusting the luminance of the frame image by combining adjustment of the exposure time of the image sensor 14 with at least one of adjustment of the light intensity of the illumination light or gain adjustment for determining the signal level of an imaging signal of the frame image obtained from the image sensor 14, while performing adjustment for reducing the RSA to be described later. Specifically, the adjustment unit 28 is configured to perform adjustment determination including determination of whether or not at least one of information regarding the motion amount between adjacent frame images of the object image in the captured image or information regarding the blurring amount of the edge of the object image in the captured image satisfies an adjustment condition, and perform the adjustment processing by adjusting the adjustment level representing the degree of strength of the adjustment processing by the magnitude of the value according to a determination result of the adjustment determination. It is also preferable that the adjustment determination includes a determination related to a dimming amount to be described later.

In such an endoscope system 1, since the image sensor 14 captures an image by the rolling shutter method as described above, in one captured frame image, the exposure timing is shifted at regular time intervals for each line or for each of a plurality of lines.

For this reason, a liquid droplet flying at a high speed may appear in the image, or the liquid may come into contact with (or adhere to) the observation window 13 to form a flow of the liquid. In this case, in the image capturing by the rolling shutter method, the edging phenomenon often occurs due to the shift of the exposure timing. Hereinafter, this edging phenomenon is referred to as rolling shutter artifact (RSA) since the artifact occurs along the line corresponding to the scanning line of the image sensor 14 in the frame image due to the rolling shutter method.

Figure 4:
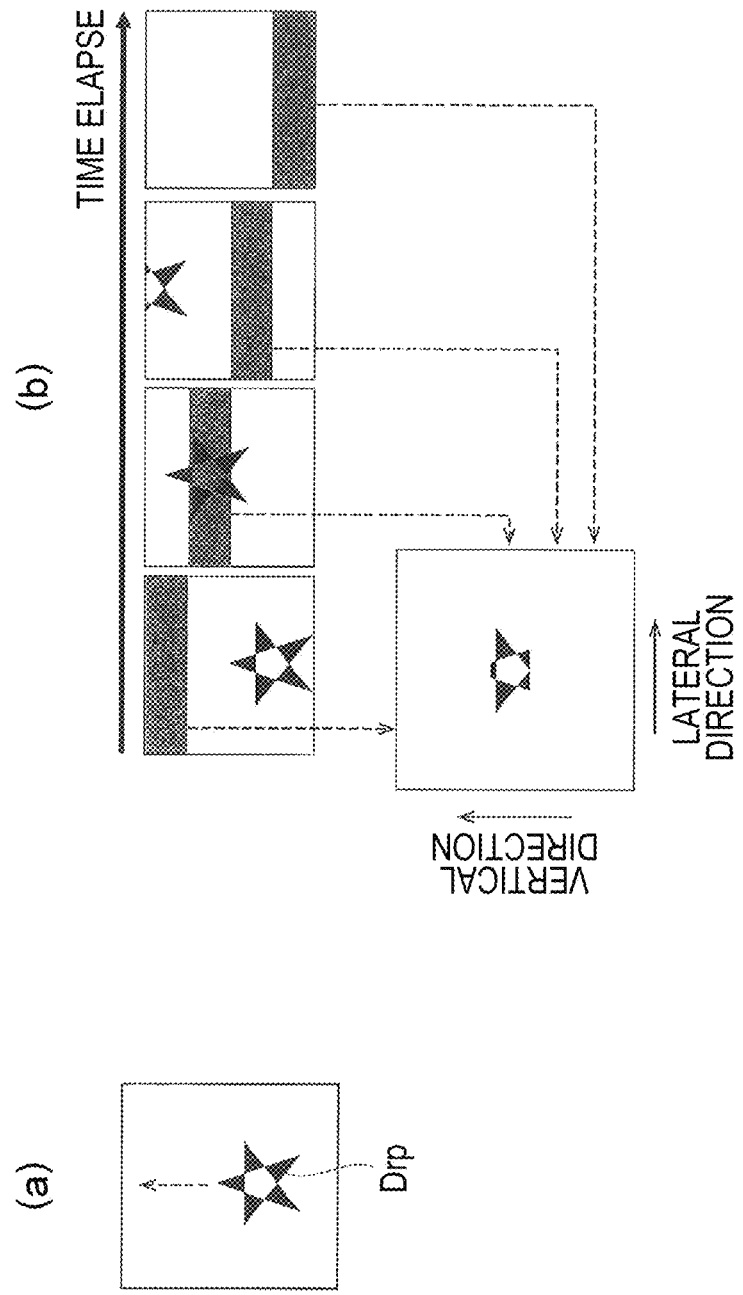
FIGS. 4(a) and 4(b) are diagrams illustrating an artifact occurring in a frame image.

FIGS. 4(*a*) and 4(*b*) are diagrams illustrating RSA occurring in the frame image. In a case where a liquid droplet Drp moves in a vertical direction of the captured image as illustrated in FIG. 4(*a*), in the rolling shutter method, as illustrated in FIG. 4(*b*), image regions of one line or a plurality of lines are sequentially exposed and imaged while shifting the exposure timing, and thus the image of the liquid droplet Drp may be interrupted along a line corresponding to the scanning line of the image sensor 14 in the frame image. This is RSA. Therefore, between adjacent lines in the vertical direction, the image is discontinuous, and an edge extending in a stripe shape is formed in the lateral direction. In a case where the liquid forms a flow without being limited to the liquid droplet Drp, an image of the biological tissue is fluctuated due to the flow of the liquid, and RSA may occur in some cases.

Note that in the example illustrated in FIG. 4(*b*), an example is described in which there is no portion where the image region of one line or a plurality of lines overlaps with the adjacent image region at the exposure timing, but the exposure timing may partially overlap with each other between the adjacent image regions.

In the endoscope system 1, examples of a case where such RSA can occur include a situation in which the surface of the observation window 13 to which a foreign substance is attached is cleaned with the liquid ejected from the air/water supply port 64 illustrated in FIG. 3, and a situation in which the distal end surface 57 comes into contact with the liquid present on the biological tissue and the liquid comes into contact with the observation window 13 and flows. Therefore, in order to predict the above-described situation in which the RSA is likely to occur before the occurrence of the RSA, the adjustment unit 28 (refer to FIG. 2) determines a situation in which the RSA is likely to occur by using an image feature amount calculated from the continuously generated frame images or a dimming amount to be described later, and performs adjustment processing for reducing the occurrence of RSA to be described later according to the determination. In the adjustment processing, the RSA can be reduced by increasing the exposure time of the image sensor 14, but the luminance of the frame image is increased due to the increasing of the exposure time. Therefore, the adjustment processing is performed by combining adjustment of the exposure time of the image sensor 14 with at least one of adjustment of the light intensity of the illumination light and gain adjustment for determining the signal level of the imaging signal of the frame image obtained from the image sensor 14. At this time, the adjustment processing is performed by adjusting the adjustment level representing the degree of strength of the adjustment processing by the magnitude of the value based on the frame image and the dimming amount.

Figure 5:
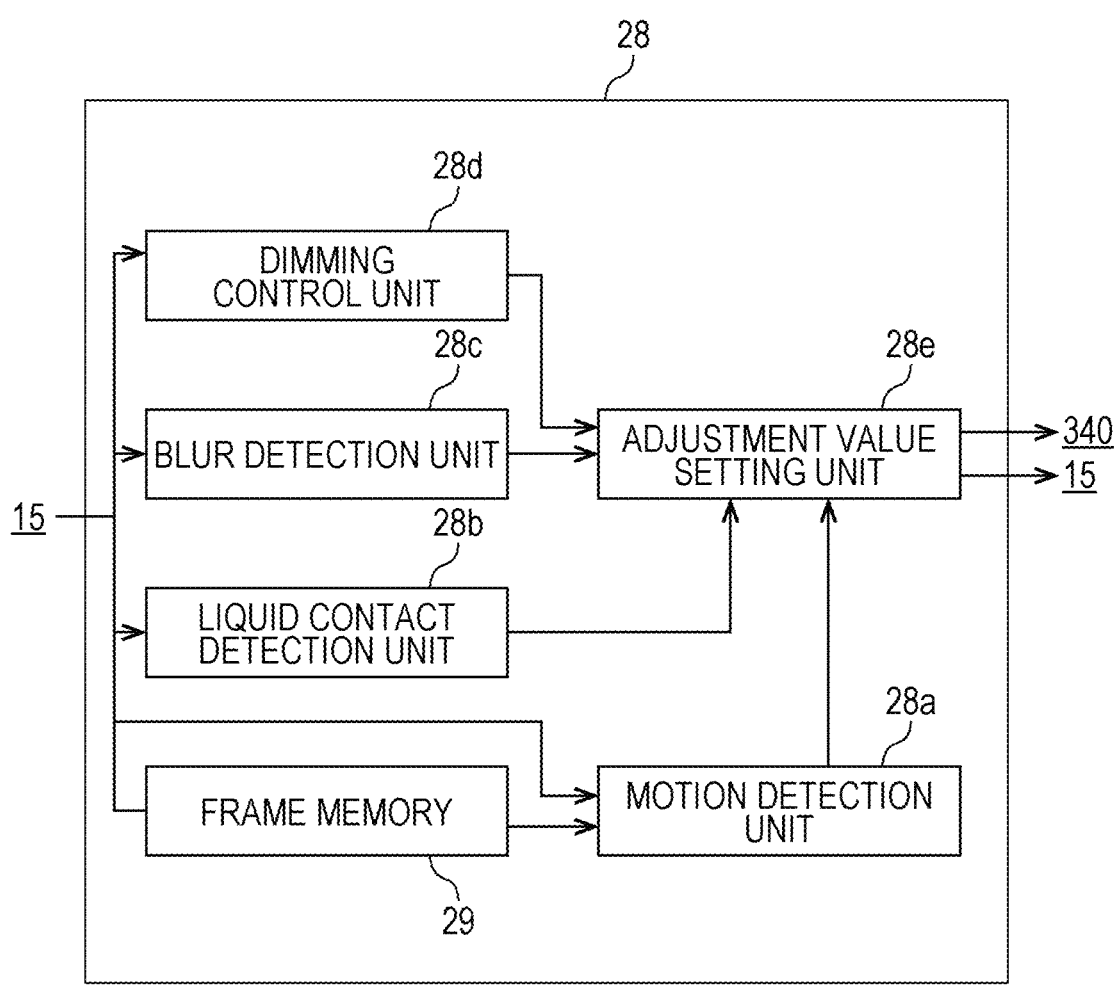
FIG. 5 is a block diagram illustrating an example of a configuration of an adjustment unit of an endoscope system according to an embodiment.

FIG. 5 is a block diagram illustrating an example of a configuration of the adjustment unit 28 of the endoscope system 1 according to the embodiment.

The adjustment unit 28 includes a frame memory 29, a motion detection unit 28*a*, a liquid contact detection unit 28*b*, a blur detection unit 28*c*, a dimming control unit 28*d*, and an adjustment value setting unit 28*e*.

The motion detection unit 28*a* is a part that detects information regarding a motion amount between the adjacent frame images of the object image in the captured image. The information regarding the motion amount includes the motion amount of the object image in the current frame image or a change amount in the motion amount of the object image in the current frame image with respect to the motion amount of the object image in the immediately previous frame image. Hereinafter, the motion amount of the object image in the current frame image will be described as an example of the information regarding the motion amount. Since the motion amount is obtained by comparison with the adjacent frame images, the immediately previous frame image to be compared with the current frame image is temporarily held in the frame memory 29, and the immediately previous frame image is read from the frame memory 29 when the current frame image is supplied. A specific description of the degree of the motion amount to be detected will be described later.

Note that, according to the embodiment, it is also preferable that the motion detection unit 28a further detect a change amount in the motion amount of the current frame image acquired by the image sensor 14 with respect to the motion amount in the immediately previous frame image as the information regarding the motion amount.

The blur detection unit 28c is a part that detects information regarding a blurring amount of an edge of the object image. The information regarding the blurring amount includes at least one of a blurring amount of an edge of the object image in the current frame image or a change amount in the blurring amount of the edge of the object image in the current frame image with respect to the blurring amount of the edge of the object image in the immediately previous frame image. A specific description of the blurring amount to be detected will be described later.

The frame image generated by the image sensor 14 includes a display region in which an image of an object is displayed, and a vignetting region in which luminance is lower than that of the display region due to the imaging optical system of the electronic scope 1 and the image of the object is not displayed, the vignetting region being formed outside the display region.

The liquid contact detection unit 28b calculates information regarding a pixel value of the vignetting region. The information regarding the pixel value of the vignetting region includes at least one of an integrated value of pixel values in the vignetting region, the number of pixels of which the pixel value in the vignetting region exceeds a predetermined threshold, a change amount in the integrated value obtained from the frame image immediately before the current frame image, or a change amount in the number of pixels obtained from the frame image immediately before the current frame image. In a case where the liquid is in contact with (or adheres to) the observation window 13, a viewing angle is widened by a refractive index of the liquid, and the pixel value of the vignetting region is greater than the pixel value of the vignetting region in a case where the liquid is not in contact with (or adheres to) the observation window 13. Therefore, it is possible to determine whether or not the liquid adheres to the observation window 13 by examining the pixel value in the vignetting region. A specific description of the vignetting region will be described later.

The dimming control unit 28d adjusts a luminance level of the frame image obtained by the image sensor 14 by using a dimming amount set to decrease the value from the currently set value in a case where the luminance level of the current frame image is greater than a target luminance level and increase the value from the currently set value in a case where the luminance level of the current frame image is less than the target luminance level, the dimming amount being a parameter for performing adjustment such that the luminance level of the current frame image acquired by the image capturing of the image sensor 14 is the target luminance level. Therefore, when acquiring the frame image, the dimming control unit 28d converts the pixel value into the luminance value, obtains the total sum of the luminance values of effective pixels (pixels other than the vignetting region), and calculates an average luminance level obtained by dividing the total sum of the luminance values by the number of the effective pixels as the current luminance level. The dimming control unit 28d changes the currently set dimming amount based on the current luminance level and the target luminance level.

According to the embodiment, a value obtained by adding log 2 (target luminance level/current luminance level)/constant (the constant is a preset value, for example, the value is set to 10) to the value of the currently set dimming amount is set as a value of the dimming amount to be newly set this time. Note that the value of the dimming amount at the time of starting the processor 200 is set to a predetermined value, for example, 50%. The value of the dimming amount of 100% means that the light intensity of the light source device 300, the exposure time of the image sensor 14, and the gain level of the image sensor 14 are maximum, and the value of the dimming amount of 0% means that the light intensity of the light source device 300, the exposure time of the image sensor 14, and the gain level of the image sensor 14 are minimum. In the following examples of the dimming amount, the value of the dimming amount is represented by 0% to 100%.

When the observation window 13 approaches the object to receive a large amount of reflected light from the object and the luminance value of the frame image increases, the dimming amount decreases. In this case, the observation window 13 comes into contact with the object, and the liquid on the object easily comes into contact with (adheres to) the observation window 13. Therefore, the change amount in the current dimming amount with respect to the immediately previous dimming amount reflects that the observation window 13 approaches the object and the liquid on the object easily comes into contact with (adheres to) the observation window 13.

Furthermore, in a case where the observation window 13 is in contact with the object or maintains a state of being extremely close to the object, the liquid on the object easily comes into contact with (adheres to) the observation window 13. Therefore, the maintaining time during which the dimming amount is maintained at a value lower than a predetermined value reflects that the liquid on the object easily comes into contact with (adheres to) the observation window 13.

Therefore, it is preferable that the dimming control unit 28d calculates, as the information regarding the dimming amount, at least one of the change amount in the current dimming amount with respect to the immediately previous dimming amount and the maintaining time for maintaining the dimming amount at a value lower than a predetermined value.

The information regarding the motion amount, the blurring amount, and the pixel value of the vignetting region described above is collectively referred to as an image feature amount. The image feature amount, the dimming amount, and the change amount in the dimming amount are used for setting an adjustment level and further an adjustment value in the dimming value setting unit 28e.

The adjustment value setting unit 28e performs the adjustment processing by adjusting the adjustment level in the adjustment processing according to the determination result of whether or not the image feature amount sent from the motion detection unit 28a, the blur detection unit 28c, and the liquid contact detection unit 28b, the dimming amount sent from the dimming control unit 28d, and the change in the dimming amount satisfy the adjustment condition. The adjustment level represents the degree of strength of the adjustment processing by the magnitude of the value, and means that the larger the value, the stronger the degree of the adjustment processing. The determination of the adjustment value setting unit 28e and the adjustment of the adjustment level will be specifically described later.

Figure 6:
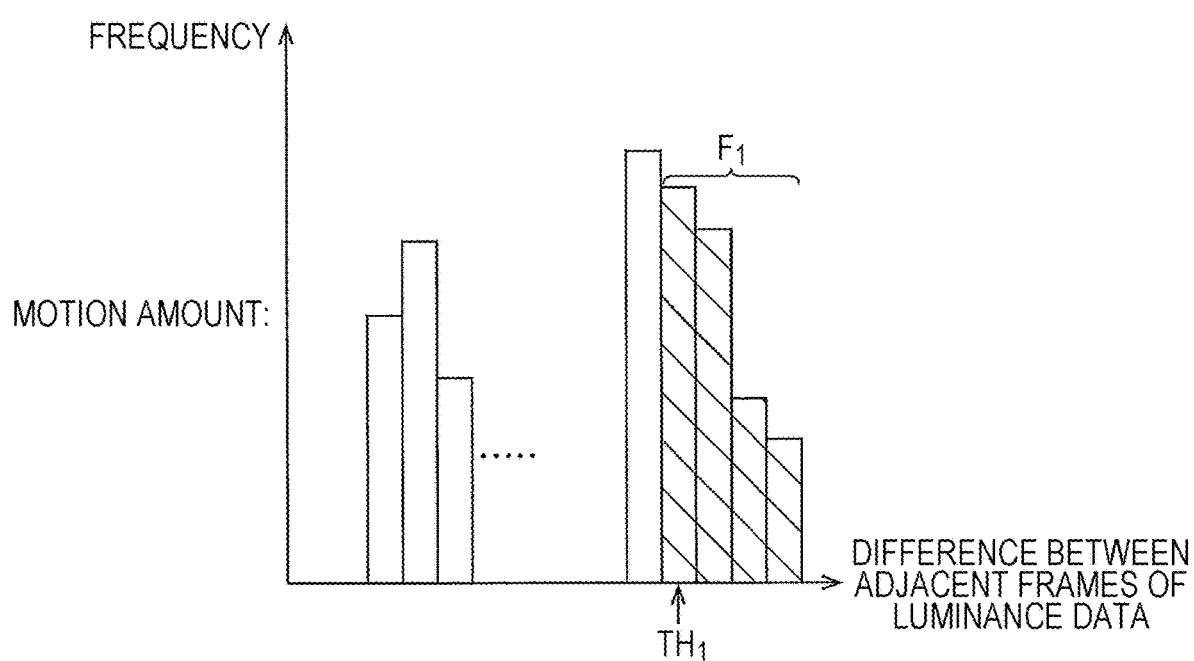
FIG. 6 is a diagram illustrating an example of a method of calculating a value indicating a degree of a motion amount in an endoscope system according to an embodiment.

FIG. 6 is a diagram illustrating an example of a method of calculating the motion amount. The motion detection unit 28a converts the pixel value of the effective pixel (pixel of a portion excluding the vignetting region) in the frame image into a luminance value, and subtracts the luminance value obtained by converting the pixel value of the effective pixel in the immediately previous frame image read from the frame memory 29 from the luminance value of the current frame image between the corresponding pixels to obtain a difference in luminance value. Moreover, the motion detection unit 28a obtains the motion amount by multiplying the number of pixels $F_1$ having a difference equal to or greater than a predetermined threshold $TH_1$ by a predetermined coefficient in a frequency distribution of the difference. The number of differences exceeding the threshold increases at an initial stage where the liquid starts to flow by coming into contact with (or adhering to) the observation window 13 or during the flow of the liquid. Therefore, in a case where the motion amount exceeds a predetermined threshold, it can be said that the RSA is likely to occur. Note that, in the above-described example, a value obtained by multiplying the number of pixels $F_1$ having a difference equal to or greater than the predetermined threshold $TH_1$ by a predetermined coefficient is obtained as the motion amount, but the method of obtaining the motion amount by using the difference between the luminance values is not limited to the above-described method.

Figure 7:
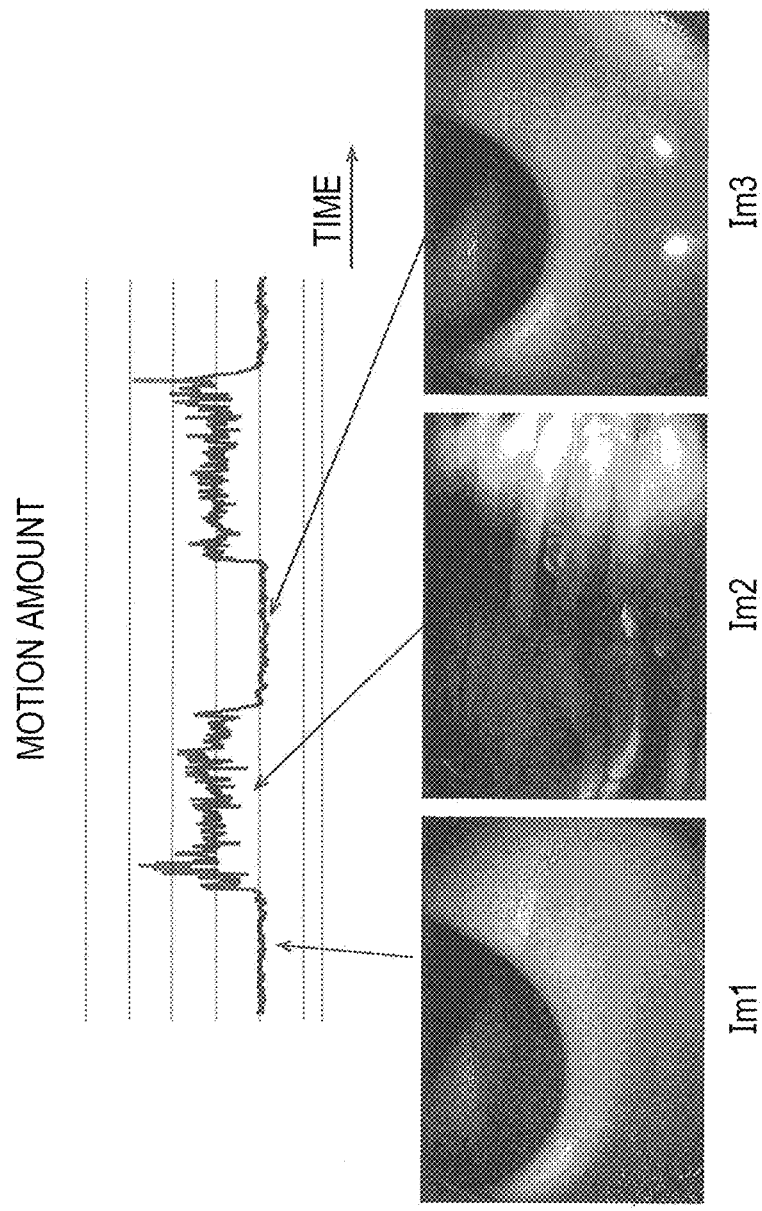
FIG. 7 is a diagram illustrating an example of a temporal change in a value indicating a degree of a motion amount calculated in the endoscope system according to an embodiment.

FIG. 7 is a diagram illustrating an example of a temporal change in the motion amount obtained by the above-described method. In a state of a photograph Im1, the motion amount is small and stable, but in a state of a photograph Im2 when water is supplied to the observation window 13 in order to clean the observation window 13, the motion amount is great and fluctuates. Thereafter, in a state of a photograph Im3 when the supply of water is stopped, the motion amount is small and stable. In this manner, the motion amount reflects presence or absence of the liquid flowing on the observation window 13.

Figure 8:
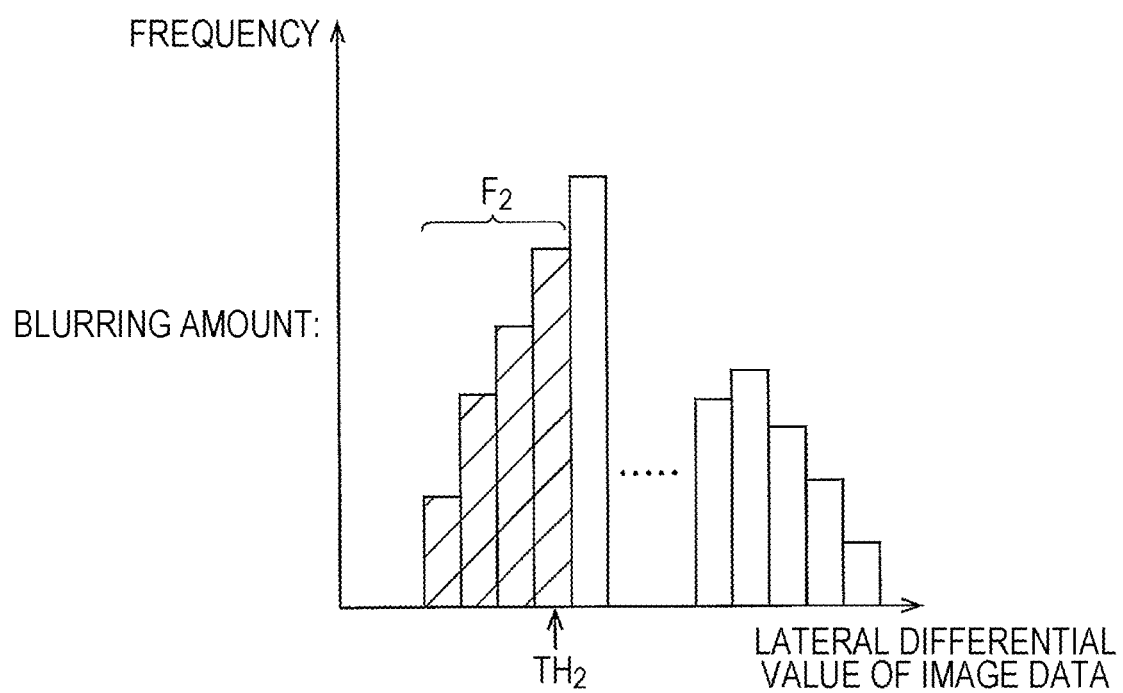
FIG. 8 is a diagram illustrating an example of a method of calculating a value indicating a degree of a blurring amount calculated in an endoscope system according to an embodiment.

FIG. 8 is a diagram illustrating an example of a method of calculating the blurring amount. The blur detection unit 28c calculates a lateral differential value representing strength of an edge extending in the vertical direction of the frame image by using a differential filter, for example, a differential filter of 5 pixels×5 pixels for each pixel of the effective pixels in the frame image. In the pixel corresponding to the edge in which the pixel value rapidly changes, the value obtained by the filtering processing increases. Moreover, the blur detection unit 28c obtains the blurring amount by multiplying the number of pixels $F_2$ having a differential value equal to or less than a predetermined threshold $TH_2$ by a predetermined coefficient in a frequency distribution of the frame image having the lateral differential value. As in the RSA, the lateral differential value does not reflect the degree of the edge extending linearly in the lateral direction and the number of generated edges, but reflects the degree of the edge extending in the vertical direction and the number of generated edges. Therefore, the blurring amount obtained based on the lateral differential value does not reflect the occurrence of the RSA extending linearly in the lateral direction. However, as in the case where the liquid is flowing on the observation window 13, the flow of the liquid causes the image of the object to have blurring or bokeh in the vertical direction and the lateral direction to reduce the edges in the vertical direction and the lateral direction. Therefore, it can be said that the smaller the number of generated edges extending in the vertical direction, the greater the blurring amount of the object image due to the flow of the liquid. Therefore, it can be said that the number of pixels $F_2$ of which the differential value is equal to or less than the threshold $TH_2$ among the lateral differential values which are not affected by the occurrence of the RSA reflects the degree of the blurring amount in which the image of the object is blurred by the flow of the liquid adhering to the observation window 13.

Figure 9:
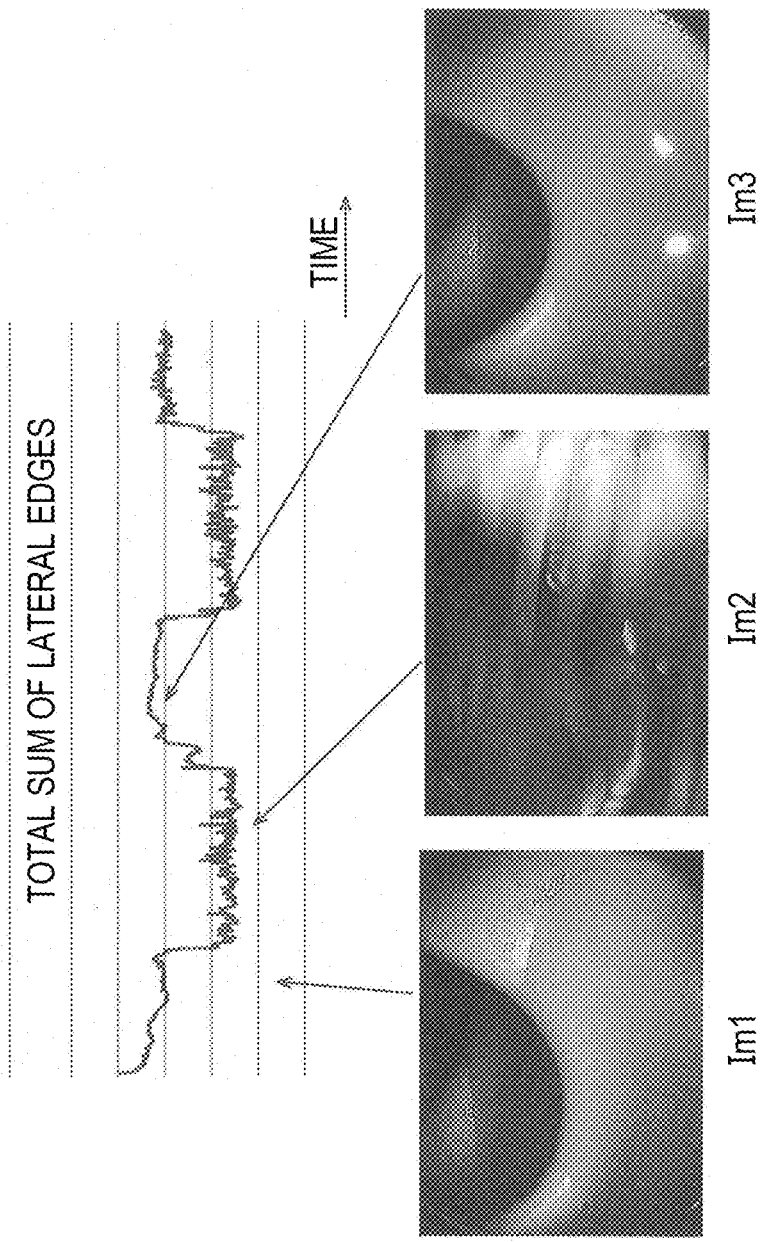
FIG. 9 is a diagram illustrating an example of a temporal change in a value of the total sum of pixels of a frame image when a differential filter for calculating a lateral differential value is applied to the frame image.

FIG. 9 is a diagram illustrating an example of a temporal change in a value of the total sum of pixels of the frame image when a differential filter for calculating a lateral differential value is applied to the frame image. In a state of a photograph Im1, the total sum of the differential values is great and stable, but in a state of a photograph Im2 when water is supplied to the observation window 13 in order to clean the observation window 13, the total sum of the differential values is small. Thereafter, in a state of a photograph Im3 when the supply of water is stopped, the total sum of the differential values is great and stable. As described above, it can be said that the smaller the total sum of the lateral differential values (the total sum of the lateral edges), the greater the blurring amount. Therefore, the blur detection unit 28c obtains a value indicating the degree of the blurring amount by multiplying the number of pixels $F_2$ having a differential value equal to or less than a predetermined threshold $TH_2$ by a predetermined coefficient in a frequency distribution of the frame image having the lateral differential value. Note that the method of calculating the blurring amount is not limited to the above-described method, and as long as the blurring amount can be set such that the value becomes smaller as the differential value increases based on the information regarding the lateral differential value, the method of calculating the blurring amount is not particularly limited.

Figure 10:
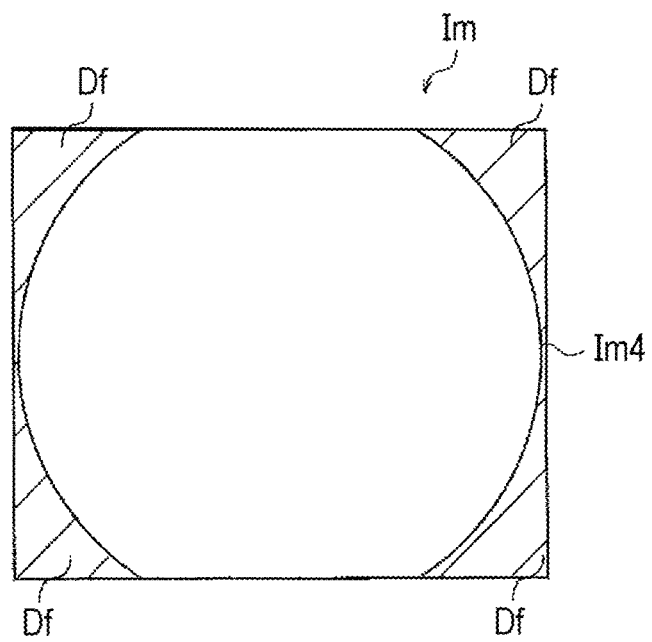
FIG. 10 is a view illustrating a vignetting region used in an endoscope system according to an embodiment.

FIG. 10 is a view illustrating the vignetting region. As illustrated in FIG. 10, a frame image Im generated by the image sensor 14 includes a circular display region Im4 in which an image of an object is displayed, and a vignetting region Df in which luminance is lower than that of the display region due to the imaging optical system of the electronic scope 1 and the image of the object is not displayed, the vignetting region Df being formed outside the display region. The vignetting region Df is formed in a predetermined range. In the example illustrated in FIG. 10, the vignetting region Df is formed at four corners of the rectangular frame image Im. The vignetting region Df is a region obtained by the imaging optical system (circular lens group) of the electronic scope 1. However, when the liquid comes into contact with (or adheres to) the observation window 13, since the liquid has a refractive index higher than that of air, the light also reaches the vignetting region Df due to the refractive index. Therefore, it is possible to determine whether or not the liquid adheres to the observation window 13 by obtaining information regarding a pixel value of the vignetting region Df.

Figure 11:
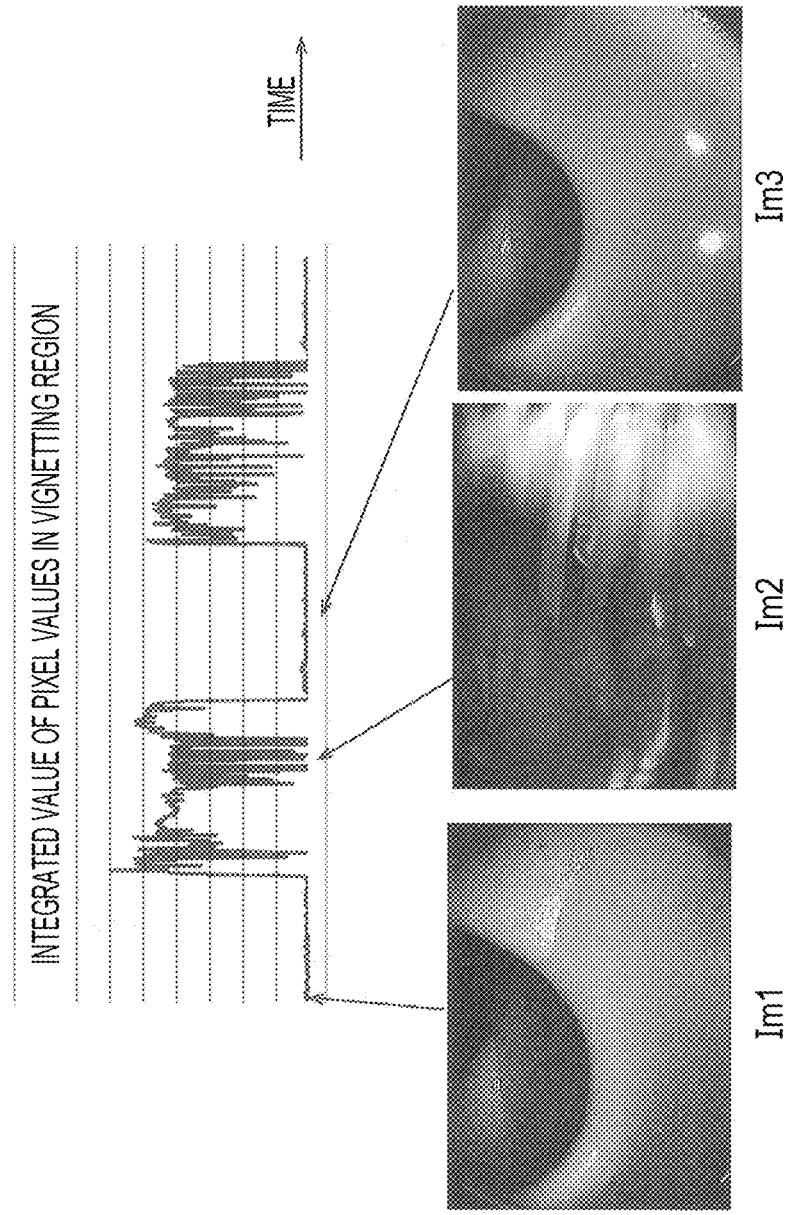
FIG. 11 is a diagram illustrating an example of a temporal change in an integrated value of pixel values of a vignetting region, which is calculated in an endoscope system according to an embodiment.

FIG. 11 is a diagram illustrating an example of a temporal change in an integrated value of pixel values, which is an example of information regarding the pixel values of the vignetting region Df. In a state of a photograph Im1, the integrated value of the pixel values in the vignetting region Df is small and stable, but in a state of a photograph Im2 when water is supplied to the observation window 13 in order to clean the observation window 13, the integrated value of the pixel values in the vignetting region Df is great. Thereafter, in a state of a photograph Im3 when the supply of water is stopped, the integrated value of the pixel values in the vignetting region Df is small and stable. In this manner, the integrated value reflects presence or absence of the liquid coming into contact with (or adhering to) the observation window 13. In the example illustrated in FIG. 11, the integrated value of the pixel values in the vignetting region Df is used as the information regarding the pixel value of the vignetting region Df. However, the number of pixels $F_1$ of which the pixel value of the vignetting region Df exceeds a predetermined threshold may be used.

Furthermore, as illustrated in FIG. 11, the integrated value of the pixel values in the vignetting region Df suddenly increases due to contact with liquid, or the number of pixels rapidly increases. Therefore, the integrated value in the current frame image Im, the integrated value of the number of pixels $F_1$ in the immediately previous frame image Im, or a change amount from the number of pixels $F_1$ is used as information regarding the image feature amount.

Furthermore, since the liquid in contact with the observation window 13 starts to flow, and the RSA is likely to occur as a flow velocity of the liquid increases, it is also preferable to calculate the change in the motion amount as the above-described image feature amount.

Moreover, the liquid on the biological tissue comes into contact with (or adheres to) the observation window 13 by bringing the distal end surface 57 of the electronic scope 100 close to the surface of the biological tissue. When the distal end surface 57 of the electronic scope 100 is brought close to the surface of the biological tissue, the luminance of the image captured by the electronic scope 100 gradually increases. Therefore, the dimming amount is gradually decreased by the above-described dimming control unit 28*d* adjusting the dimming amount. Therefore, in a case where the change in the dimming amount set for the current frame image from the dimming amount set for the immediately previous frame image is negative and an absolute value of the change amount is greater than a predetermined threshold, it can be said that the observation window 13 comes into contact with the liquid on the biological tissue and thus the RSA is likely to occur. Therefore, the dimming control unit 28*d* preferably calculates a change amount in the dimming amount set for the current frame image from the dimming amount set for the immediately previous frame image.

Information regarding such an image feature amount and the change amount in the dimming amount are sent to the adjustment value setting unit 28*e*.

Figure 12:
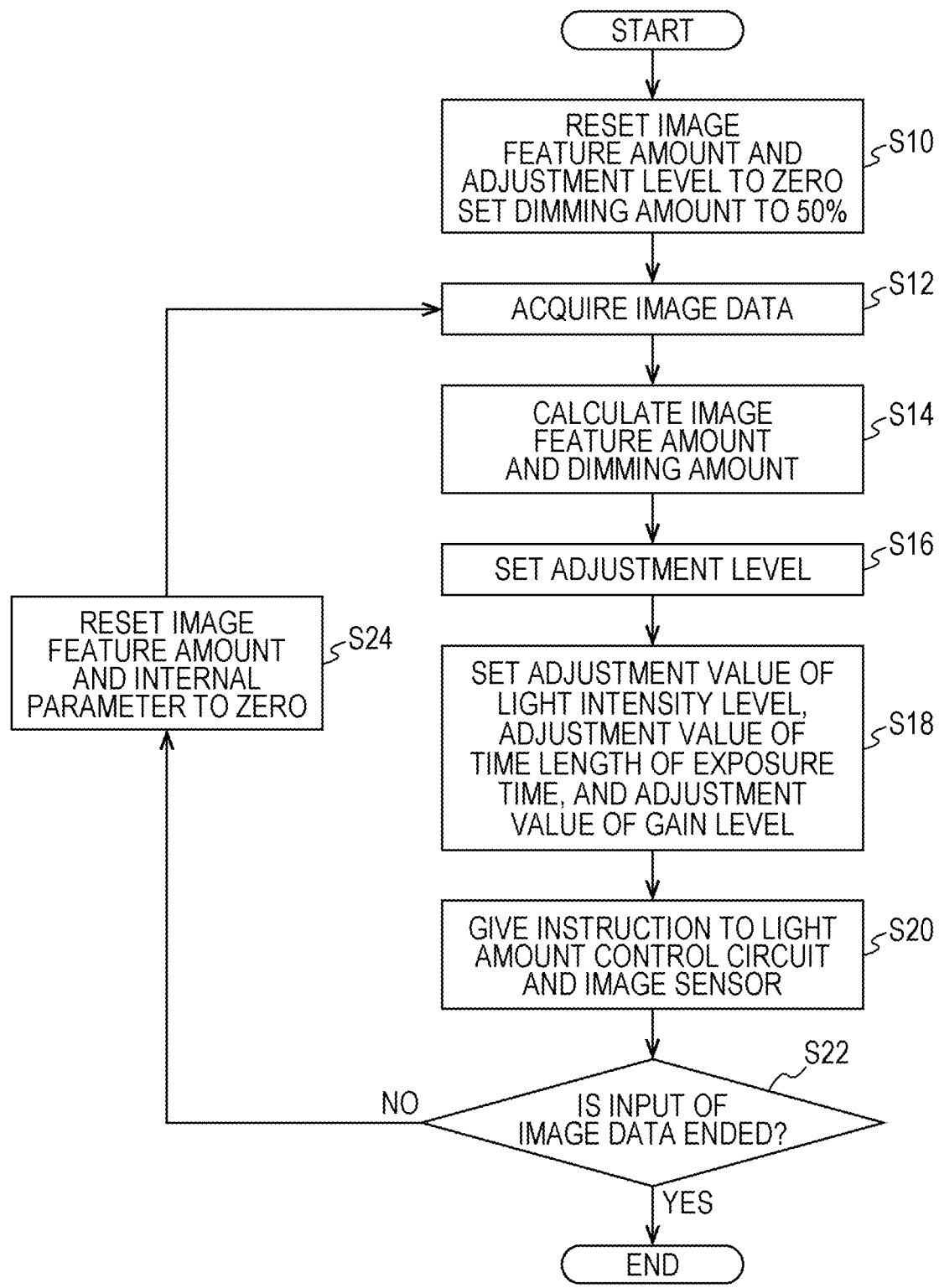
FIG. 12 is a flowchart illustrating an example of a flow of adjustment processing performed by an endoscope system according to an embodiment.

FIG. 12 is a flowchart illustrating an example of a flow of adjustment processing performed by the endoscope system 1 according to the embodiment. First, when the endoscope system 1 is started, the adjustment unit 28 resets the image feature amount and the adjustment level indicating the degree of strength of the adjustment processing to zero, and sets the dimming amount to 50% (step S10). Thereafter, the object is imaged by the image sensor 14, so that the adjustment unit 28 acquires image data of a frame image (step S12). When the adjustment unit 28 acquires the image data, the motion detection unit 28*a*, the blur detection unit 28*c*, the liquid contact detection unit 28*b*, and the dimming control unit 28*d*, of the adjustment unit 28, calculate the image feature amounts and the dimming amount as described above (step S14).

Next, the adjustment value setting unit 28*e* sets an adjustment level indicating strength of processing in the adjustment processing for reducing RSA and adjusting the luminance of the image (step S14). The adjustment level is set according to a value of the image feature amount and change in the dimming amount. Setting of the adjustment level will be described later.

Moreover, the adjustment value setting unit 28*e* sets, based on the set adjustment level and dimming amount, an adjustment value of a light intensity level of the illumination light radiated by the light source unit 310, the adjustment value of a length of the time of the exposure performed by the image sensor 14, and the adjustment value of a gain level for determining a signal level of the imaging signal generated by the image sensor 14 (step S18).

The values of the set light intensity level, the set length of the exposure time, and the set gain level are sent to the system controller 21, and the system controller 21 creates control signals regarding the light intensity level, the length of the exposure time, and the gain level. This control signal is sent to the light amount control circuit 340 and the image sensor 14, and an instruction on the values of the light intensity level, the length of the exposure time, and the gain level are given to the light amount control circuit 340 and the image sensor 14. The gain adjustment based on the gain level is performed on a gain of an amplifier (not illustrated) built in the image sensor 14.

The adjustment unit 28 determines whether or not the input of the image data has ended (step S22), and ends the setting of the adjustment value in a case where it is determined that the input of the image data has ended. On the other hand, in a case where it is determined that the input of the image data to the adjustment unit 28 has not ended, that is, in a case where it is determined that the next frame image is acquired, the image feature amount and various internal parameters are reset to zero (step S24), and new image data is acquired (step S12). As described above, each time the image data is input, the adjustment level and the adjustment value are set.

Figure 13:
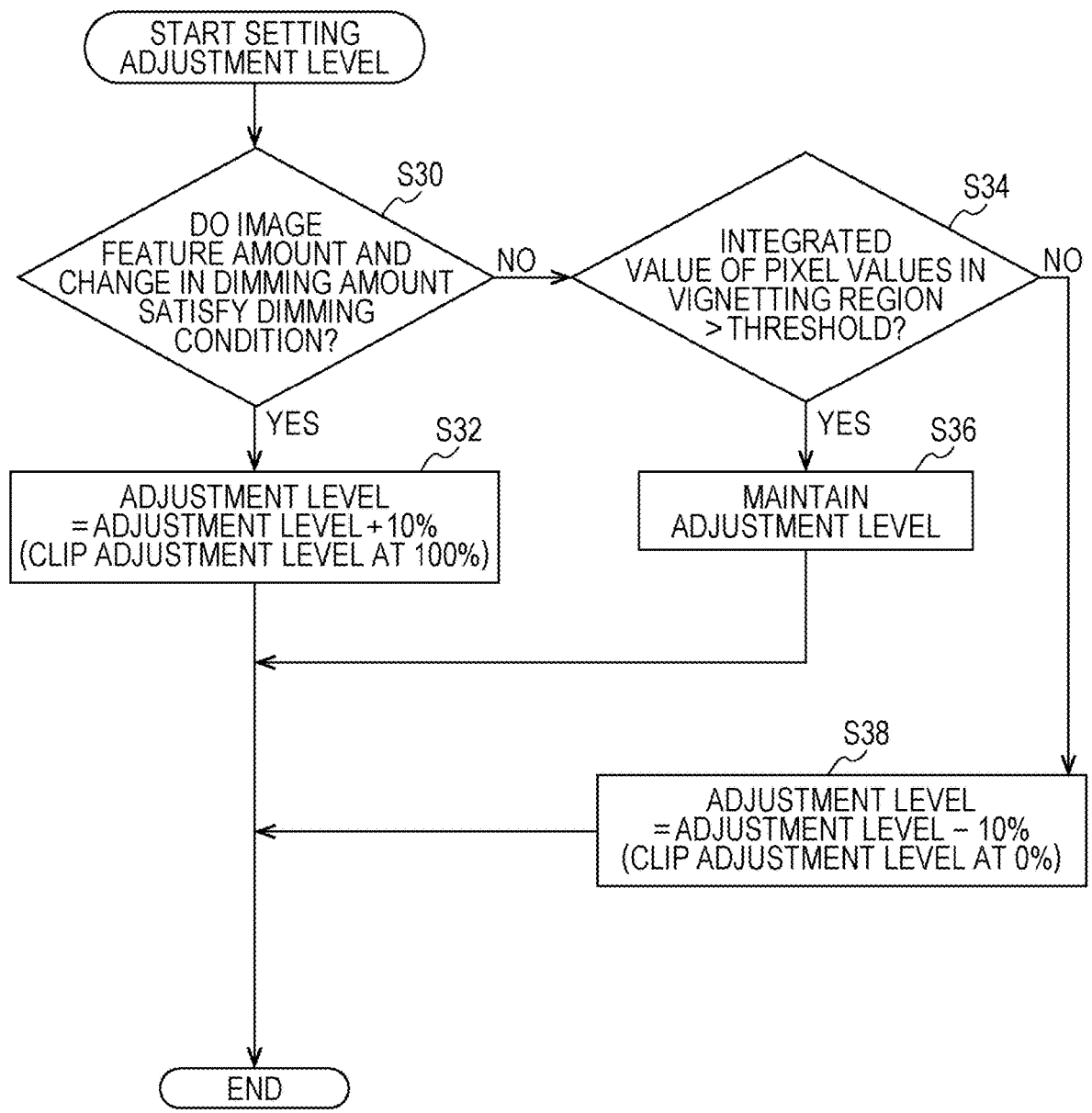
FIG. 13 is a flowchart illustrating an example of a flow of setting an adjustment level in step S16 illustrated in FIG. 12.

FIG. 13 is a flowchart illustrating an example of a flow of setting the adjustment level in step S16 illustrated in FIG. 12.

The adjustment value setting unit 28*e* determines whether or not information regarding the image feature amount such as the motion amount, the change in the motion amount (difference obtained by subtracting the motion amount in the immediately previous frame image from the motion amount in the current frame image), and the blurring amount, and the change amount in the dimming amount (difference obtained by subtracting the dimming amount set in the immediately previous frame image from the dimming amount set in current frame image) satisfy a preset adjustment condition (performs adjustment determination) (step S30). The adjustment condition is set for each of the motion amount, the change in the motion amount, the blurring amount, and the change amount in the dimming amount. For example, the adjustment value setting unit 28*e* determines whether or not the motion amount is greater than a preset first threshold, whether or not the blurring amount is greater than a preset second threshold, whether or not the change in the motion amount is greater than a preset third threshold, and whether or not the change amount in the dimming amount is negative and the absolute value of the change amount in the dimming amount is greater than a preset fifth threshold.

In addition to such determination, the change amount in the blurring amount and the maintaining time for maintaining the dimming amount at a value lower than a predetermined value may be used for determination of the adjustment condition.

In such a plurality of determinations, in a case where any one of the determinations is affirmative, the adjustment value setting unit 28e sets a value obtained by adding 10% to the currently set adjustment level as a new adjustment level (step S32). Note that in the adjustment determination, in a case where the determination for at least one of a plurality of pieces of information to be determined is affirmative, the processing of step S32 is performed, but in a case where at least two of a plurality of pieces of the information to be determined satisfy the adjustment condition, the processing of step S32 may be performed.

Furthermore, the adjustment level is expressed in % display as a value indicating the degree of strength of the adjustment processing. The adjustment level is a value in which the strength of the adjustment processing is set by setting the case where the adjustment processing is not performed at all as 0% and the case where the adjustment processing is performed most strongly as 100%. Note that the adjustment level is set to zero when the endoscope system 1 is started.

On the other hand, in a case where all the determinations are negative in step S30 (the determination result of the adjustment determination is negative), the adjustment value setting unit 28e determines whether or not the integrated value of the pixel values in the vignetting region Df is greater than a predetermined fourth threshold (step S34). In a case where the integrated value of the pixel values in the vignetting region Df is greater than a predetermined sixth threshold, there is an extremely high possibility that the RSA occurs, and thus the adjustment level of the adjustment processing for reducing the RSA is maintained (step S36). In a case where it is determined that the integrated value of the pixel values in the vignetting region Df is equal to or less than the predetermined fourth threshold, the adjustment value setting unit 28e sets, as a new adjustment level, a value in which the RSA occurs but the number of times of the occurrences of the RSA is small or the value obtained by subtracting 10% from the adjustment level when the RSA does not occur (step S38).

As described above, the adjustment value setting unit 28e sets the adjustment level based on the image adjustment amount and the change in the dimming amount. Note that in the determination in step S34, the integrated value of the pixel values in the vignetting region Df is used. However, instead of the integrated value, the number of pixels $F_1$ of which the pixel value of the vignetting region Df exceeds a threshold may be used.

Figure 14:
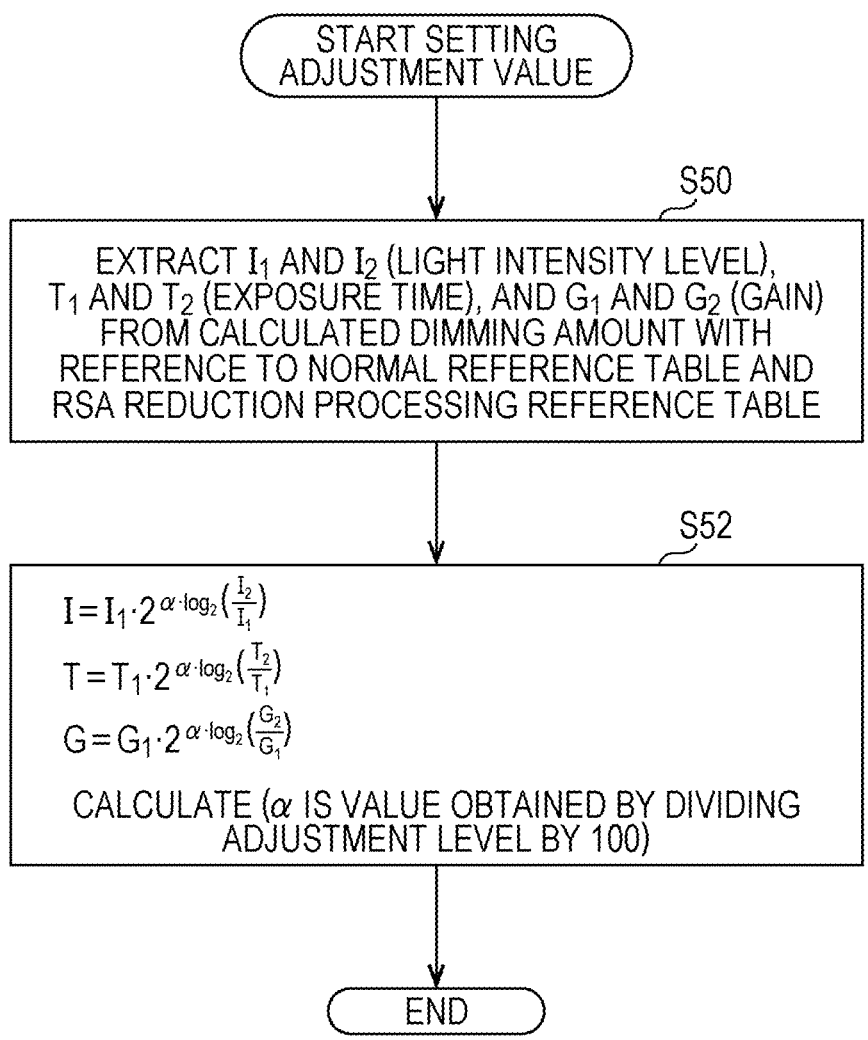
FIG. 14 is a flowchart illustrating an example of a flow of setting an adjustment value in step S18 illustrated in FIG. 12.

FIG. 14 is a flowchart illustrating an example of a flow of setting an adjustment value in step S18 illustrated in FIG. 12.

By using a first set value of each of the light intensity level, the exposure time, and the gain level in a case where the adjustment processing is performed at the adjustment level of 0%, that is, in a case where the adjustment processing is not performed at all, and a second set value of each of the light intensity level, the exposure time, and the gain level in a case where the adjustment processing is performed at the adjustment level of 100%, the adjustment value setting unit 28e determines the adjustment value of the level of the light intensity, the adjustment value of the time length of the exposure time, and the adjustment value of the gain level by performing interpolation according to the adjustment level between the first set value and the second set value.

That is, the adjustment value setting unit 28e extracts a light intensity level $I_1$, an exposure time $T_1$, and a gain $G_1$, which are the first set values, from a normal reference table, and extracts a light intensity level $I_2$, an exposure time $T_2$, and a gain $G_2$, which are the second set values, from a RSA reduction processing reference table, based on the dimming amount sent from the dimming control unit 28d with reference to a non-adjustment processing reference table (first reference table, hereinafter, referred to as normal reference table) in a case where the adjustment processing as the RSA reduction processing is not performed and an RSA reduction processing reference table (second reference table) (step S50). In each of the normal reference table and the RSA reduction reference table, the correspondence relationship of the light intensity level, the exposure time, and the gain with respect to the dimming amount is determined. The correspondence relationship represents a change in the light intensity level, the exposure time, and the gain with respect to a change in the dimming amount. FIG. 15(*a*) is a diagram illustrating an example of the normal reference table, and FIG. 15(*b*) is a diagram illustrating an example of the RSA reduction reference table. In FIGS. 15(*a*) and 15(*b*), the light intensity level, the exposure time, and the gain level, which are set in advance, are standardized as a reference, and expressed in % display.

As can be seen from FIGS. 15(*a*) and 15(*b*), the change in the exposure time and the light intensity level with respect to the dimming amount is different between the normal reference table and the RSA reduction processing reference table. In the RSA reduction processing reference table, the exposure time is made longer than the corresponding exposure time in the normal reference table in order to reduce the occurrence of the RSA in a portion where the dimming amount is small. However, since the luminance of the image is increased by increasing the exposure time, the light intensity level is decreased in order to suppress an increase in luminance. Note that in the illustrated example, the gain level is substantially the same between the normal reference table and the RSA reduction reference table, but the exposure time, the light intensity level, and the gain level may be different between the normal reference table and the RSA reduction reference table. In this case, it is preferable that the products of the exposure time, the light intensity level, and the gain level are set to be the same between the normal reference table and the RSA reduction reference table from the viewpoint of preventing the luminance level in the image from changing even when the adjustment processing is performed.

The adjustment value setting unit 28e sets values of a light intensity level I, an exposure time T, and a gain G by performing interpolation according to the adjustment level between the extracted light intensity level $I_1$, exposure time $T_1$, and gain $G_1$, and the extracted light intensity level $I_2$, exposure time $T_2$, and gain $G_2$ (step S52).

When an equation illustrated in step S52 of FIG. 14 is modified, for example, the light intensity level I becomes $I=I_1^{(1-\alpha)} \cdot I_2^{\alpha}$ ($\alpha$ is a value obtained by dividing the adjustment level by 100). That is, $I=I_1$ is obtained in a case where the adjustment level $\alpha=0$ (the adjustment processing is not performed), and $I=I_2$ is obtained in a case where the adjustment level $\alpha=1$ (the adjustment processing is performed with the maximum intensity). In a case where the adjustment level $\alpha$ is greater than zero and less than 1, the index according to $I_1$ and $I_2$ is allocated by the adjustment level $\alpha$, and an interpolated value is set.

Therefore, according to the embodiment, it is preferable that the adjustment level $\alpha$ has a higher value as the degree of the adjustment processing is stronger, and the adjustment value approaches the light intensity level $I_2$, the exposure time $T_2$, and the gain $G_2$ (second set value) as the value of the adjustment level $\alpha$ is higher.

Information of the values of the light intensity level I, exposure time T, and gain G set in this manner is transmitted to the light amount control circuit 340 and the image sensor 14 as control signals.

In the endoscope system 1, the adjustment unit 28 of the processor 200 is configured to perform adjustment processing of adjusting the luminance of the frame image by combining adjustment of the exposure time of the image sensor 14, and at least one of adjustment of the light intensity of the illumination light or gain adjustment, perform adjustment determination including determination of whether or not at least one of information regarding the motion amount between adjacent frame images of the object image in the captured image or information regarding the blurring amount of the edge of the object image satisfies an adjustment condition, and perform the adjustment processing by adjusting the adjustment level representing the degree of strength of the adjustment processing for RSA reduction by the magnitude of the value according to a determination result of the adjustment determination. Therefore, the adjustment processing for RSA reduction can be performed before the occurrence of the RSA. Moreover, since the adjustment level is adjusted based on information regarding at least the motion amount of the object image or information regarding the blurring amount of the object image in the image, it is possible to efficiently perform the adjustment processing of suppressing the occurrence of the RSA by adding the strength of the adjustment processing according to the adjustment level. The motion amount or the blurring amount of the object image tends to increase immediately before or in a case where the liquid comes into contact with the observation window 13, and can be effectively used as an index for predicting the occurrence of the RSA.

Moreover, the adjustment unit 28 is configured to determine the information regarding the blurring amount of the edge of the object image and the information regarding the motion amount of the object image, and adjust the adjustment level according to the determination results, such that it is possible to determine a situation in which the RSA can occur without missing. For example, the adjustment condition related to the motion amount is, for example, whether or not the motion amount exceeds the first threshold. For example, the adjustment condition related to the blurring amount of the edge is, for example, whether or not the blurring amount exceeds the second threshold.

Note that it is preferable that the information regarding the motion amount includes at least one of the motion amount of the object image in the current frame image or a change amount in the motion amount of the object image in the current frame image with respect to the motion amount of the object image in the immediately previous frame image. Furthermore, it is preferable that the information regarding the blurring amount includes at least one of a blurring amount of the object image in the current frame image or a change amount in the blurring amount of the object image in the current frame image with respect to the blurring amount of the object image in the immediately previous frame image. According to this, the adjustment unit 28 can determine the situation in which the RSA can occur without missing. The adjustment condition related to the change amount in the motion amount or the change amount in the blurring amount is, for example, whether or not the change amount in the motion amount or the change amount in the blurring amount exceeds a threshold.

Furthermore, as described above, the adjustment unit 28 is preferably configured to adjust the adjustment level according to at least the determination result for the information regarding the dimming amount. Since the adjustment unit 28 adjusts the luminance level of the image obtained by the image sensor 14 by using the dimming amount, the luminance level can be efficiently achieved as the target luminance level. When the distal end surface 72 approaches the object to the extent that the observation window 13 comes into contact with (or adheres to) the liquid on the biological tissue, the adjustment unit 28 decreases the dimming amount such that the luminance level of the frame image does not increase. Therefore, it is preferable to adjust the adjustment level on the assumption of such a case. That is, it is determined whether or not the change amount in the current dimming amount (the dimming amount set for the current frame image) with respect to the immediately previous dimming amount (the dimming amount set for the immediately previous frame image) satisfies the adjustment condition, and the adjustment unit 28 is configured to adjust the adjustment level according to the determination result for the information regarding the motion amount or the blurring amount and the determination result for the change amount in the dimming amount. The adjustment condition related to the change amount in the dimming amount is, for example, whether or not the change amount in the dimming amount is negative and an absolute value of the change amount in the dimming amount is greater than the fifth threshold.

Furthermore, in a case where the observation window 13 comes into contact with the object or maintains the state of being extremely close to the object, it is preferable to calculate at least one of the maintaining times for maintaining the dimming amount at a value lower than a predetermined value in consideration of the fact that the liquid on the object is likely to come into contact with (adhere to) the observation window 13 as described above.

According to this, the adjustment unit 28 can determine the situation in which the RSA can occur without missing.

The adjustment unit 28 determines whether or not the information regarding the pixel value in the vignetting region Df satisfies the adjustment condition in addition to the determination for the information regarding the motion amount or the blurring amount, and the adjustment unit 28 adjusts the adjustment level according to at least the determination result for the information regarding the pixel value in the vignetting region Df separately from the determination result for the information regarding the motion amount or the blurring amount. Therefore, the adjustment unit 28 can determine the situation in which the RSA can occur without missing. It is preferable that the information regarding the pixel value of the vignetting region Df includes at least one of an integrated value of pixel values in the vignetting region Df, the number of pixels $F_1$ of which the pixel value in the vignetting region Df exceeds a predetermined threshold, a change amount in the integrated value obtained from the frame image immediately before the current frame image, or a change amount in the number of pixels $F_1$ obtained from the frame image immediately before the current frame image. The adjustment condition related to the integrated value of the pixel values in the vignetting region Df is, for example, whether or not the integrated value is greater than the fourth threshold.

As described above, every time the frame image is obtained from the image sensor 14, the adjustment unit 28 performs adjustment determination by using the adjustment condition as in step S30 illustrated in FIG. 13, and in a case where the adjustment determination is affirmative, for example, in a case where the determination for at least one of a plurality of pieces of information to be determined is affirmative, the value of the adjustment level is made greater than the value of the adjustment level determined in the immediately previous frame image as in step S32 illustrated in FIG. 13. Therefore, the adjustment level can be sequentially adjusted according to the frame image.

In a case where the determination result of the adjustment determination in step S30 by the adjustment unit 28 is negative and the integrated value of the pixel values in the vignetting region Df is greater than the predetermined fourth threshold, the adjustment value setting unit 28e maintains the value of the adjustment level at the value of the adjustment level determined in the immediately previous frame image. Therefore, the adjustment level can be appropriately maintained according to the frame image.

Furthermore, in a case where the determination result of the adjustment determination in step S30 by the adjustment unit 28 is negative and the integrated value of the pixel values in the vignetting region Df is equal to or less than the fourth threshold, the value of the adjustment level in the current frame image is made smaller than the value of the adjustment level determined in the immediately previous frame image. Therefore, the adjustment level can be sequentially adjusted according to the frame image.

Figure 16:
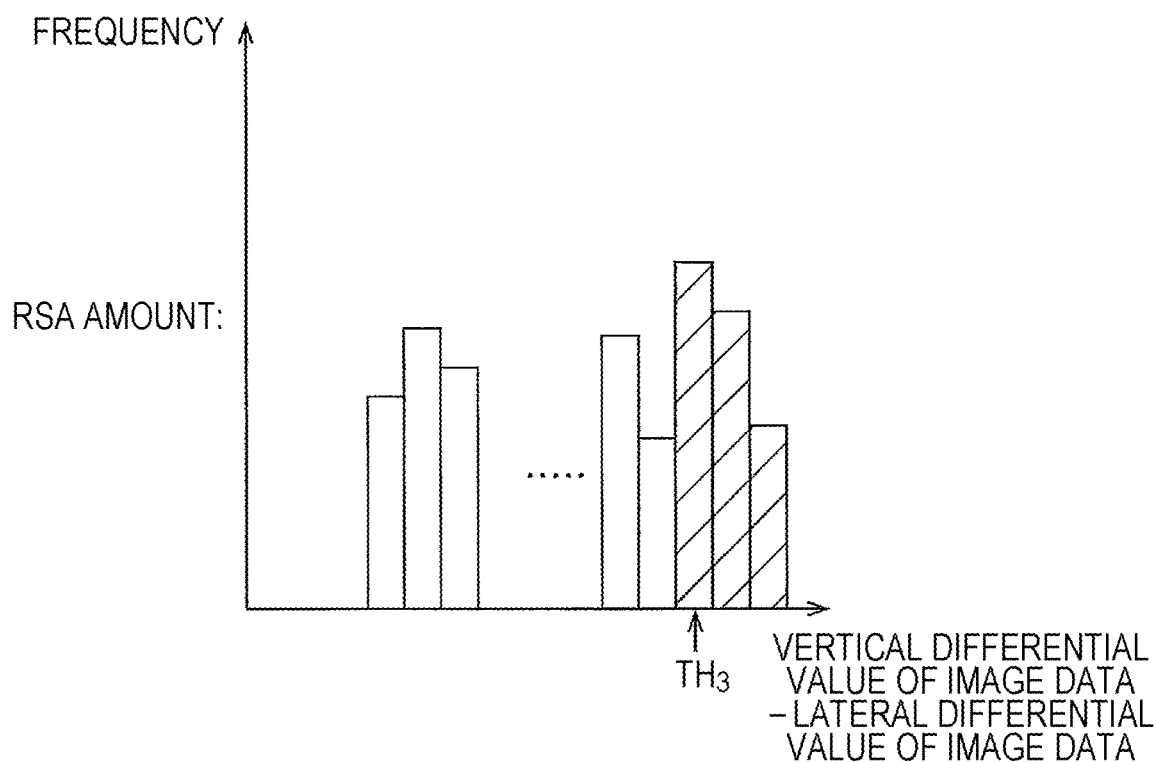
FIG. 16 is a diagram illustrating an example of a method of calculating an RSA amount calculated in an endoscope system according to an embodiment.

Note that in the flow illustrated in FIG. 13, in step S34, the determination is performed by calculating the integrated value of the pixel values in the vignetting region Df and comparing the integrated value with the fourth threshold, but instead of the integrated value, the occurrence amount of the RSA occurring in the frame image (hereinafter, referred to as RSA amount) may be compared with a preset seventh threshold, and the processing of step S36 may be performed in a case where the RSA amount is greater than the seventh threshold, and the processing of step S38 may be performed in a case where the RSA amount is equal to or less than the seventh threshold. FIG. 16 is a diagram illustrating an example of a method of calculating the RSA amount.

In the example illustrated in FIG. 16, in the frequency distribution of the value obtained by subtracting the lateral differential value from a vertical differential value in each pixel of the frame image, a value obtained by multiplying the total number of pixels having values equal to or greater than a threshold $TH_3$ by a predetermined coefficient is defined as the RSA amount. The vertical differential value reflects the blurring of the object image in the vertical direction in addition to the edge of the RSA. The lateral differential value reflects the blurring of the frame image in the lateral direction without reflecting the edge of the RSA. Here, assuming that the blurring in the vertical direction is substantially the same as the blurring in the lateral direction, a value obtained by subtracting the lateral differential value from the vertical differential value is used in order to remove the blurring in the vertical direction.

Such an RSA amount can be used instead of the integrated value of the pixel values in the vignetting region Df of step S34 illustrated in FIG. 13.

Figure 17:
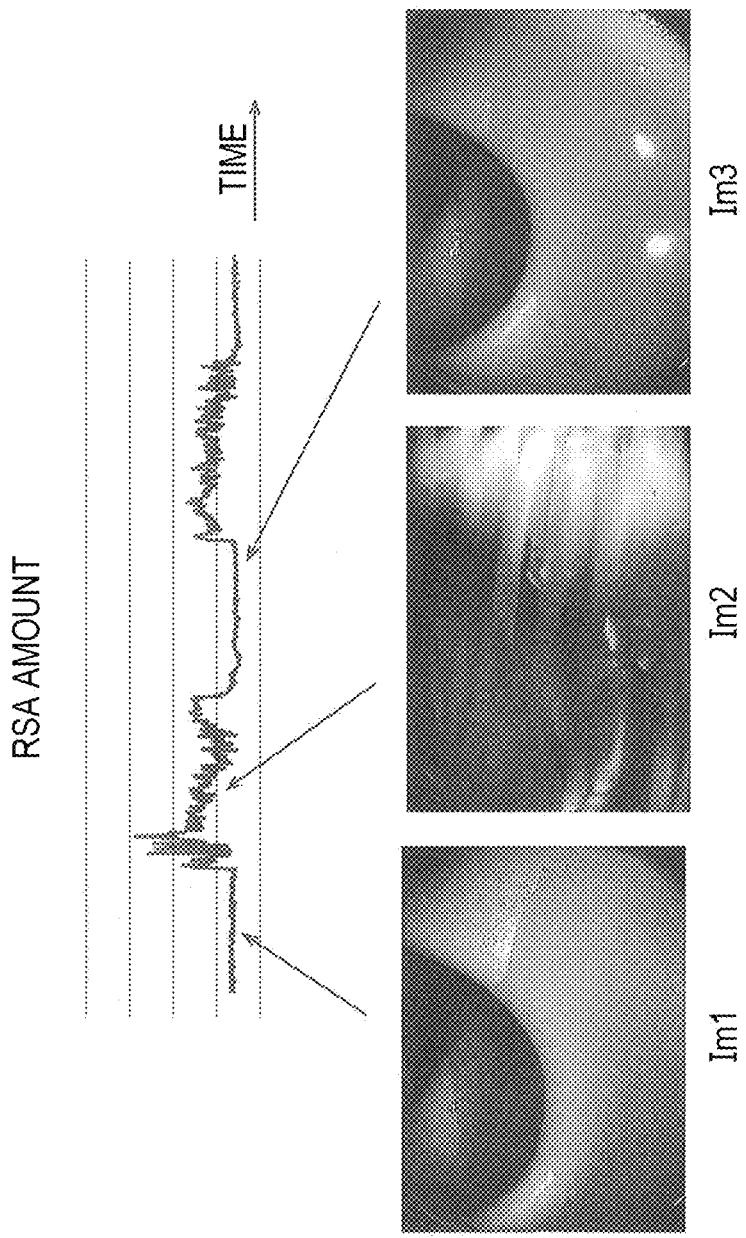
FIG. 17 is a diagram illustrating an example of a temporal change in an RSA amount calculated in an endoscope system according to an embodiment.

FIG. 17 is a diagram illustrating an example of a temporal change in the RSA amount obtained by the above-described method. In a state of a photograph Im1, the value of the RSA amount is small and stable, but in a state of a photograph Im2 when water is supplied to the observation window 13 in order to clean the observation window 13, the value of the RSA amount is great and fluctuates. Thereafter, in a state of a photograph Im3 when the supply of water is stopped, the value of the RSA amount is small and stable. As described above, the value of the RSA amount reflects the number of times of the occurrence of the RSA.

Therefore, according to the embodiment, the adjustment unit 28 preferably includes an RSA detection unit (index calculation unit) that calculates an RSA amount that is an index indicating the degree of occurrence of the RSA in the frame image, and the adjustment unit 28 preferably maintains the value of the adjustment level at the value of the adjustment level determined in the immediately previous frame image as in step S36 illustrated in FIG. 13 in a case where the determination result in step S30 illustrated in FIG. 13 is negative and the RSA amount is greater than the predetermined seventh threshold. According to this, the adjustment level can be maintained according to the frame image.

Furthermore, in a case where the determination result in step S30 illustrated in FIG. 13 is negative and the RSA amount is equal to or less than the predetermined seventh threshold, the adjustment unit 28 preferably sets the value of the adjustment level in the current frame image to be smaller than the value of the adjustment level determined in the immediately previous frame image as in step S38 illustrated in FIG. 13. According to this, the adjustment level can be sequentially maintained according to the frame image.

As described above, in a case where the RSA amount is detected, the adjustment unit 28 can adjust the adjustment level by using the following configuration of the adjustment unit 28 and perform the adjustment processing for reducing the RSA.

Figure 18:
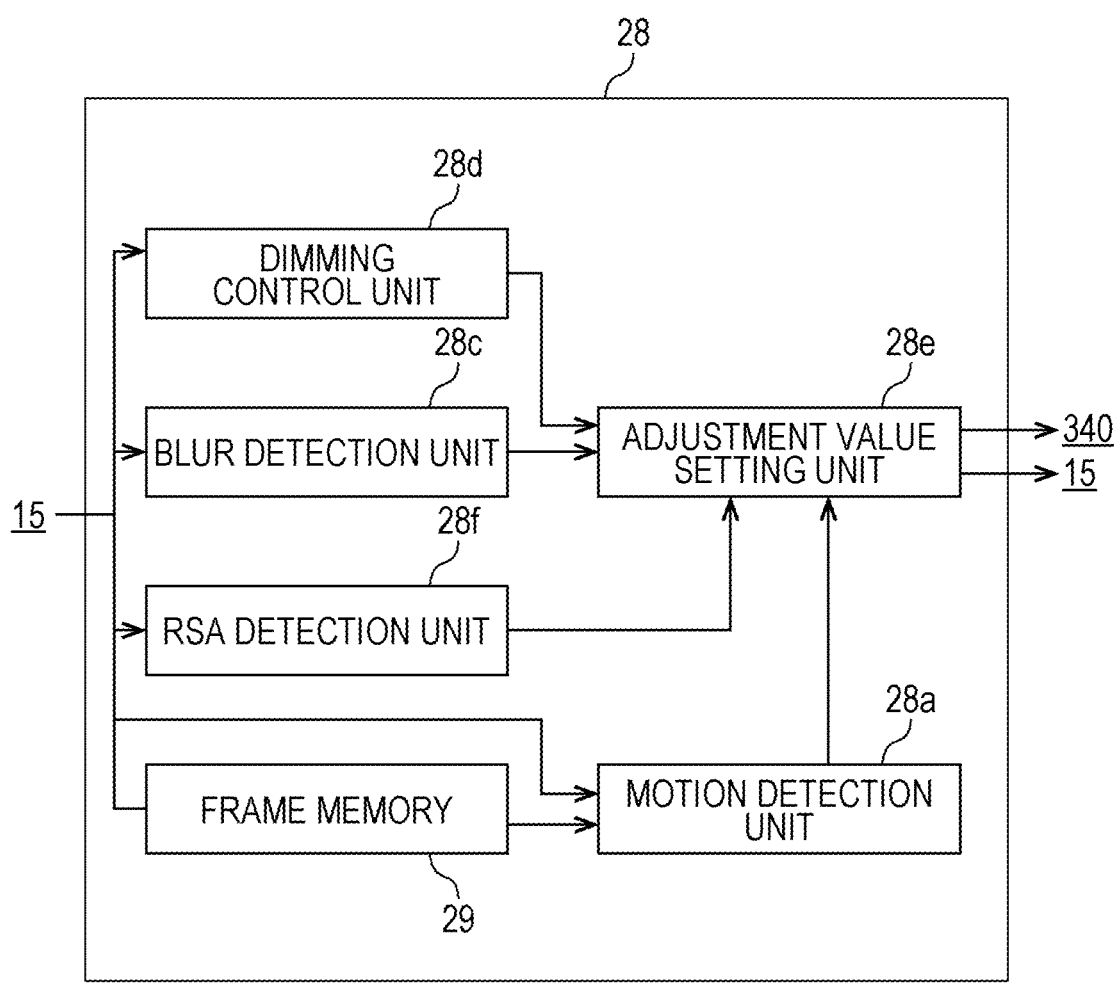
FIG. 18 is a block configuration diagram of an adjustment unit in an endoscope system according to an embodiment.

FIG. 18 is a block configuration diagram of the adjustment unit 28 according to the embodiment different from the adjustment unit 28 illustrated in FIG. 5. The adjustment unit 28 illustrated in FIG. 18 includes an RSA detection unit 28f instead of the liquid contact detection unit 28b illustrated in FIG. 5, and the other components are the same as those of the adjustment unit 28 illustrated in FIG. 5. Therefore, in FIG. 18, description of the dimming control unit 28d, the blur detection unit 28c, the frame memory 29, and the motion detection unit 28a is omitted.

The RSA detection unit 28f is a part (index calculation unit) that calculates an RSA amount which is an index indicating the degree of the occurrence amount of the RSA in the frame image. The RSA detection unit 28f calculates the RSA amount by, for example, the method illustrated in FIG. 16. The calculated RSA amount is sent to the adjustment value setting unit 28e. The adjustment value setting unit 28e is a part that performs adjustment processing of adjusting the luminance of the frame image by combining adjustment of the exposure time of the image sensor 14 with at least one of adjustment of the light intensity of the illumination light and gain adjustment for determining a signal level of an imaging signal of the frame image obtained from the image sensor 14. Specifically, the adjustment value setting unit 28 is configured to perform the adjustment processing by adjusting the adjustment level representing the degree of strength of the adjustment processing by the magnitude of the value according to the determination result for whether or not the RSA amount satisfies the adjustment condition. In this case, determination of whether or not the image feature amount sent from the motion detection unit 28a satisfies the adjustment condition and whether or not the change amount in the dimming amount sent from the dimming control unit 28d satisfies the adjustment condition may be determined together with determination of whether or not the RSA amount satisfies the adjustment condition. The adjustment condition related to the RSA amount is whether or not the RSA amount is greater than an eighth threshold.

In this case, as in step S30 illustrated in FIG. 13, in a case where all the determinations of whether or not the image feature amount satisfies the adjustment condition, whether or not the change amount in the dimming amount sent from the dimming control unit 28d satisfies the adjustment condition, and whether or not the RSA amount satisfies the adjustment condition are denied, instead of the determination in step S34 illustrated in FIG. 13 for determining whether or not the integrated value of the pixel values in the vignetting region is greater than the fourth threshold, it is preferable to determine whether or not the RSA amount is greater than the seventh threshold.

Figure 19:
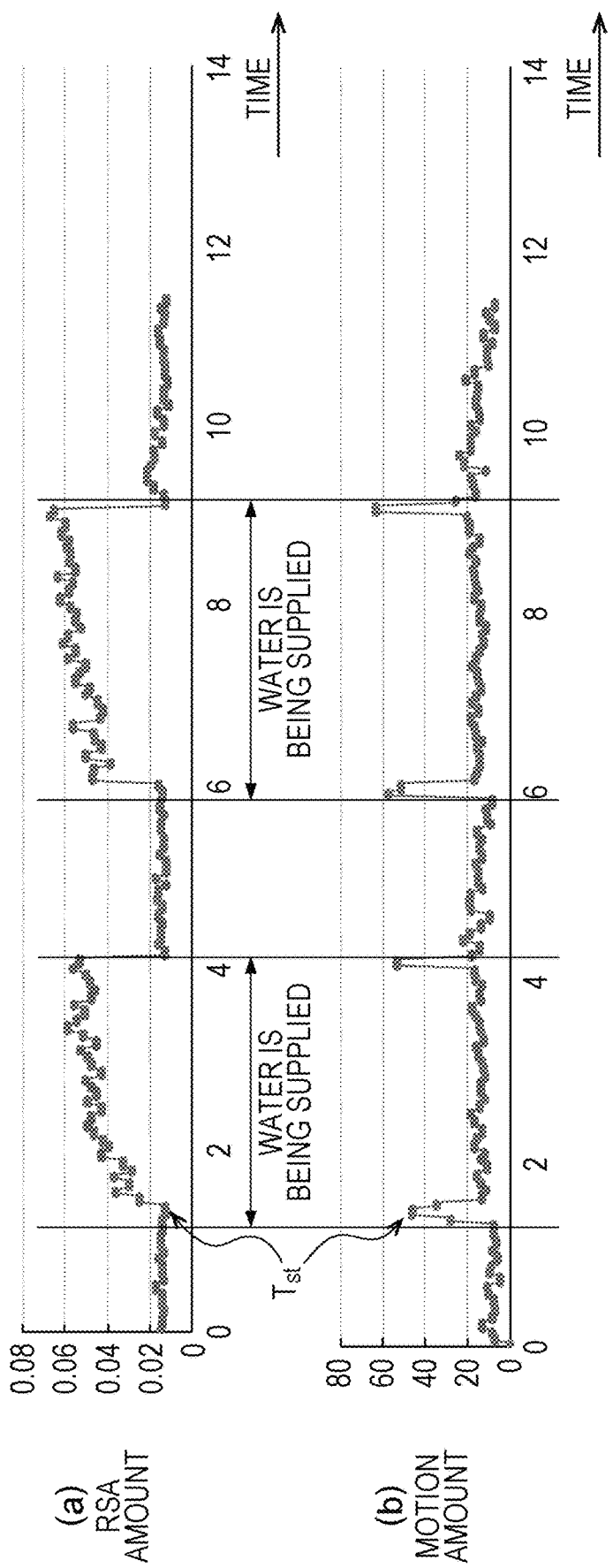
FIG. 19(a) is a diagram illustrating an example of a temporal change in an RSA amount calculated in an endoscope system according to an embodiment.
FIG. 19(b) is a diagram illustrating an example of a temporal change in a motion amount calculated in the endoscope system according to the embodiment.

FIG. 19(a) is a diagram illustrating an example of a temporal change in a value indicating the RSA amount, and FIG. 19(b) is a diagram illustrating an example of a temporal change in a value of the motion amount. FIG. 19(a) and FIG. 19(b) respectively illustrate the temporal change in the RSA amount when cleaning water is supplied to the observation window 13 and the temporal change in the motion amount of the object image. In an initial stage Tst in which the supply of the cleaning water is started, and then the water comes into contact with the observation window 13 to form a flow, the RSA amount does not increase, but the motion amount increases by reflecting the motion of the object image caused by the contact of water. On the other hand, after the initial stage Tst, the RSA amount increases, but the motion amount decreases since the motion of the object image is stabilized. As described above, the RSA amount becomes a large value obtained when the occurrence of the RSA continues. Therefore, it can be determined whether or not the RSA is likely to occur due to the motion amount before the RSA occurs, and in a case where the RSA occurs and continues, the RSA amount can be used as an index of whether to maintain the adjustment level of the adjustment processing or to decrease the adjustment level.

Figure 20:
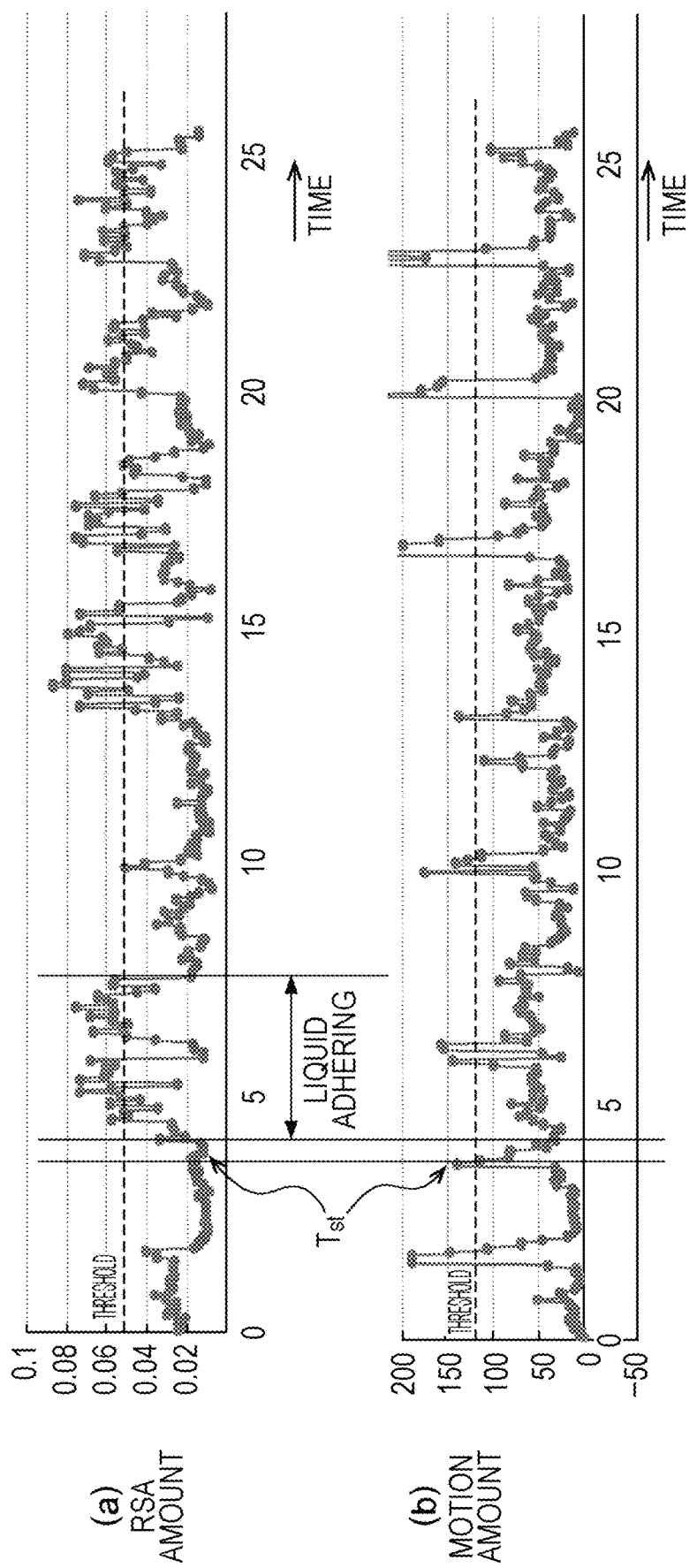
FIG. 20(a) is a diagram illustrating an example of a temporal change in an RSA amount calculated in an endoscope system according to an embodiment.
FIG. 20(b) is a diagram illustrating an example of a temporal change in a motion amount calculated in the endoscope system according to the embodiment.

FIG. 20(a) is a diagram illustrating an example of a temporal change in the RSA amount, and FIG. 20(b) is a diagram illustrating an example of a temporal change in the motion amount. FIG. 20(a) and FIG. 20(b) respectively illustrate the temporal change in the RSA amount when the observation window 13 approaches the biological tissue as the object and the liquid existing on the biological tissue comes into contact with the observation window 13 and the temporal change in the motion amount of the object image. Even in this case, in the initial stage Tst, the RSA amount does not increase, but the motion amount increases by reflecting the motion of the object image caused by the adhesion of the liquid. On the other hand, after the initial stage Tst, the RSA amount increases, but the motion amount relatively decreases since the motion of the object image is stabilized.

Figure 21:
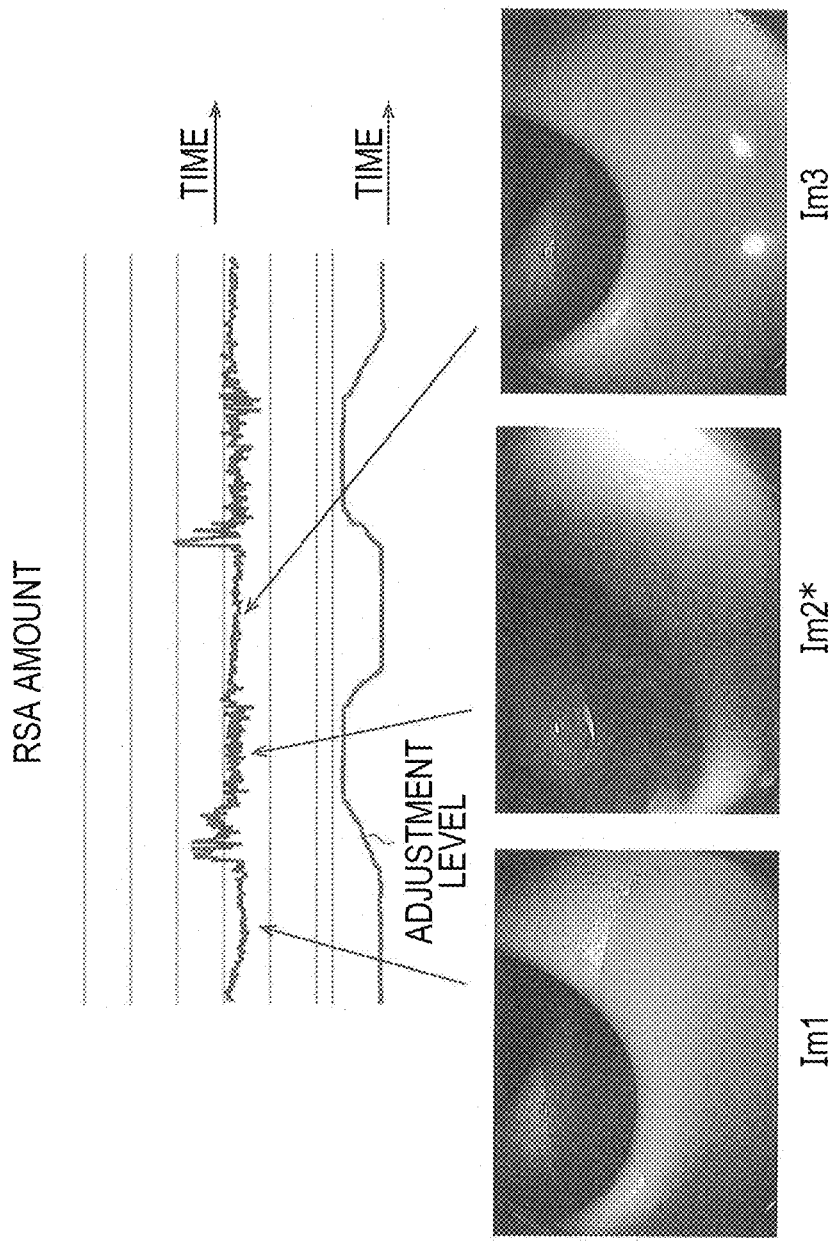
FIG. 21 is a diagram illustrating an example of a temporal change in an RSA amount and an adjustment level calculated in an endoscope system according to an embodiment.

FIG. 21 is a diagram illustrating an example of the temporal changes of the RSA amount when the adjustment processing of the embodiment is performed using the adjustment unit 28 illustrated in FIG. 18 and the adjustment level. In a state of a photograph Im1, the RSA amount is small and stable without occurrence of the RSA. In this state, when the water is supplied to the observation window 13 to clean the observation window 13, the RSA occurs and the RSA amount starts to increase, and the adjustment processing is performed at an adjustment level that gradually increases according to this. Therefore, the occurrence of the RSA in the object image can be suppressed as illustrated in a photograph Im2*. Thereafter, in a state of a photograph Im3 when the supply of water is stopped, the RSA does not occur and the RSA amount becomes small. According to this, the adjustment level gradually decreases. As described above, in the photograph Im2*, since the adjustment level is set and the adjustment processing is performed by combining the exposure time and at least one of the light intensity level or the gain level, it can be seen that the luminance level in the photograph Im2* is maintained at substantially the same level as the luminance levels of the photographs Im1 and Im3.

In this manner, it is configured to perform the adjustment processing by adjusting the adjustment level according to the determination result for whether or not the RSA amount satisfies the adjustment condition, and thus the adjustment level can be variously adjusted corresponding to the occurrence of the RSA.

As examples are illustrated in FIGS. 15(a) and 15(b), the adjustment value setting unit 28e includes a normal reference table (first reference table) and an RSA reduction reference table (second reference table) which determine the level of the light intensity, the time length of the exposure time, and the gain level of the gain adjustment with respect to the dimming amount.

Here, according to the embodiment, the products obtained by multiplying each value of the level of the light intensity, the time length of the exposure time, and the gain level of the gain adjustment with respect to the value of the dimming amount coincide with each other between the normal reference table and the RSA reduction reference table over the entire range of the possible value of the dimming amount, and the correspondence relationship of the level of the light intensity with respect to the value of the dimming amount and the correspondence relationship of the time length of the exposure time with respect to the value of the dimming amount are different from each other between the normal reference table and the RSA reduction reference table. In other words, the change in the level of the light intensity and the time length of the exposure time with respect to the change in the dimming amount is different between the normal reference table and the RSA reduction reference table, and the value of the level of the light intensity and the time length of the exposure time are different from each other.

According to the embodiment, the adjustment value setting unit 28e extracts a first set value of each of the level of the light intensity, the time length of the exposure time, and the gain level, which are determined from the normal reference table (reference table illustrated in FIG. 15(a)) according to the value of the dimming amount, and a second set value of each of the level of the light intensity, the time length of the exposure time, and the gain level, which are determined from the RSA reduction reference table (reference table illustrated in FIG. 15(b)) according to the value of the dimming amount. By using the first set value and the second set value, interpolation is performed according to the adjustment level between the first set value and the second set value corresponding to the first set value, the adjustment value of the level of the light intensity, the adjustment value of the time length of the exposure time, and the adjustment value of the gain level, which are used in the adjustment processing, are determined. Therefore, the adjustment value corresponding to the adjustment level can be set. In a case where the adjustment level is 0%, the first set value set by the normal reference table is the adjustment value.

In this manner, the interpolation is performed between the first set value and the second set value according to the adjustment level, and thus the adjustment processing can be performed with an appropriate strength. Moreover, the products obtained by multiplying each value of the level of the light intensity, the time length of the exposure time, and the gain level of the gain adjustment coincide with each other between the normal reference table and the RSA reduction reference table over the entire range of possible values of the dimming amount. Therefore, even when the adjustment processing is performed, the change in the luminance level of the image is not caused.

According to the embodiment, in the normal reference table and the RSA reduction reference table, the product obtained by multiplying each value of the light intensity level, the time length of the exposure time, and the gain level at the maximum value of the dimming amount is preferably greater than the product obtained by multiplying each value of the light intensity level, the time length of the exposure time, and the gain level at the minimum value of the dimming amount. In a case where the dimming amount is the maximum value, the luminance level of the image is extremely low. Therefore, in order to adjust the luminance level of the image in a short time, the product obtained by multiplying each value of the light intensity level, the time length of the exposure time, and the gain level is preferably great. In a case where the dimming amount is the minimum value, the luminance level of the image is extremely high, and thus the product obtained by multiplying each value of the light intensity level, the time length of the exposure time, and the gain level is preferably small. At that time, the time length of the exposure time in the RSA reduction reference table is not shorter than the time length of the corresponding exposure time in the normal reference table over the entire range of possible values of the dimming amount. At this time, it is preferable that the product of the value of the light intensity level and the value of the gain level in the RSA reduction reference table is not greater than the product of the value of the corresponding light intensity level and the value of the corresponding gain level in the normal reference table over the entire range of possible values of the dimming amount from the viewpoint that the luminance level of the frame image is not changed by the presence or absence of the adjustment processing and the adjustment level in the adjustment processing.

In the adjustment processing for reducing the RSA, the time length of the exposure time is increased to suppress the RSA in many cases as the adjustment level increases. Therefore, in order to prevent the luminance level from being increased by the adjustment processing for increasing the time length of the exposure time, the product of the value of the light intensity level and the value of the gain level in the RSA reduction reference table is preferably smaller than the product of the value of the corresponding light intensity level and the value of the corresponding gain level in the normal reference table over the entire range of possible values of the dimming amount.

According to the embodiment, it is preferable that the normal reference table and the RSA reduction reference table have a range of the dimming amount in which the time length of the exposure time of the RSA reduction reference table is longer than the time length of the exposure time of the normal reference table with respect to the value of the dimming amount, and the level of the light intensity of the RSA reduction reference table is smaller than the level of the light intensity of the normal reference table, from the viewpoint that the luminance level of the frame image is not changed by the change in the adjustment level in the adjustment processing.

Hitherto, the endoscope system of the present invention has been described in detail. The present invention is not limited to the above-described embodiment. As a matter of course, various improvements or modifications may be made within the scope not departing from the concept of the present invention.

REFERENCE SIGNS LIST

1 Endoscope system
11 LCB
12 Illumination window
13 Observation window
14 Image sensor
15 Driver signal processing circuit
21 System controller
24 Operation panel
26 Image processing unit
28 Adjustment unit
28a Motion detection unit
28b Liquid contact detection unit
28c Blur detection unit
28d Dimming control unit
28e Adjustment value setting unit
28f RSA detection unit
29 Frame memory
50 Operation unit
51 Cable
52 Operation unit
54 Insertion portion
56 Distal tip
57 Distal end surface
58 Flexible tube
60 Bending portion
62 Treatment tool opening
64 Air/water supply port
200 Processor
300 Light source device
310 Light source unit
340 Light amount control circuit
350 Condenser lens
400 Monitor

The invention claimed is:

1. An endoscope system that displays a captured image of a biological tissue in a body cavity on a screen, the endoscope system comprising:
a light source device configured to generate illumination light illuminating the biological tissue;
an electronic endoscope including an image sensor configured to capture the biological tissue as a moving image by a rolling shutter method;
a processor including an image processing unit configured to perform image processing on a frame image obtained by image capturing of the image sensor, and an adjustment unit that is a part performing adjustment processing of adjusting luminance of the frame image by combining adjustment of an exposure time of the image sensor with at least one of adjustment of light intensity of the illumination light and gain adjustment for determining a signal level of an imaging signal of the frame image obtained from the image sensor, the adjustment unit being configured to perform adjustment determination including determination of whether or not at least one of first information regarding a motion amount between adjacent frame images of an object image in the captured image or second information regarding a blurring amount of an edge of the object image in the captured image satisfies an adjustment condition, and perform the adjustment processing by adjusting an adjustment level representing a degree of strength of the adjustment processing by a magnitude of a value according to a determination result of the adjustment determination; and a monitor configured to display the frame image subjected to the image processing on the screen, wherein:

the frame image includes a display region in which the object image is displayed, and a vignetting region in which luminance is lower than that of the display region due to an imaging optical system of the electronic endoscope, the object image is not displayed, the vignetting region being formed outside the display region, and the adjustment unit further determines whether or not fourth information regarding a pixel value in the vignetting region satisfies the adjustment condition.

2. The endoscope system according to claim 1, wherein the first information regarding the motion amount includes at least one of the motion amount of the object image in a current frame image or a change amount in the motion amount of the object image in the current frame image with respect to the motion amount of the object image in an immediately previous frame image.

3. The endoscope system according to claim 1, wherein the second information regarding the blurring amount includes at least one of the blurring amount of the object image in a current frame image or a change amount in the blurring amount of the object image in the current frame image with respect to the blurring amount of the object image in an immediately previous frame image.

4. The endoscope system according to claim 1, wherein the fourth information regarding a pixel value of the vignetting region includes at least one of an integrated value of pixel values in the vignetting region, the number of pixels of which the pixel value in the vignetting region exceeds a predetermined threshold, a change amount in the integrated value obtained from the frame image immediately before a current frame image, or a change amount in the number of pixels obtained from the frame image immediately before the current frame image.

5. The endoscope system according to claim 4, wherein in a case where the determination result of the adjustment determination by the adjustment unit is negative and the integrated value of the pixel values in the vignetting region or the number of the pixels is greater than a predetermined threshold, a value of the adjustment level is maintained at a value of the adjustment level determined in the immediately previous frame image.

6. The endoscope system according to claim 4, wherein in a case where the determination result of the adjustment determination by the adjustment unit is negative and the integrated value of the pixel values in the vignetting region or the number of the pixels is equal to or less than the predetermined threshold, a value of the adjustment level in the current frame image is made smaller than a value of the adjustment level determined in the immediately previous frame image.

7. The endoscope system according to claim 1, wherein the adjustment unit performs the adjustment determination every time the frame image is obtained from the image sensor, and in a case where the determination result of the adjustment determination is affirmative, the adjustment unit makes a value of the adjustment level greater than a value of the adjustment level determined in an immediately previous frame image.

8. The endoscope system according to claim 7, wherein the adjustment unit performs a plurality of determinations as the adjustment determination, and in a case where the determination result of at least one determination or at least two determinations among a plurality of the determinations is affirmative, the determination result of the adjustment determination is affirmative.

9. The endoscope system according to claim 1, wherein the adjustment unit includes an index calculation unit that calculates an index indicating a degree of an occurrence amount of an artifact that occurs along a line corresponding to a scanning line of the image sensor due to the rolling shutter method in the frame image, and in a case where the determination result of the adjustment determination by the adjustment unit is negative and the index is greater than a predetermined threshold, a value of the adjustment level is maintained at a value of the adjustment level determined in an immediately previous frame image.

10. The endoscope system according to claim 9, wherein in a case where the determination result of the adjustment determination by the adjustment unit is negative and the index is equal to or less than a predetermined threshold, a value of the adjustment level in a current frame image is made smaller than a value of the adjustment level determined in the immediately previous frame image.

11. An endoscope system that displays a captured image of a biological tissue in a body cavity on a screen, the endoscope system comprising:

a light source device configured to generate illumination light illuminating the biological tissue;

an electronic endoscope including an image sensor configured to capture the biological tissue as a moving image by a rolling shutter method;

a processor including an image processing unit configured to perform image processing on a frame image obtained by image capturing of the image sensor, and an adjustment unit that is a part performing adjustment processing of adjusting luminance of the frame image by combining adjustment of an exposure time of the image sensor with at least one of adjustment of light intensity of the illumination light and gain adjustment for determining a signal level of an imaging signal of the frame image obtained from the image sensor, the adjustment unit being configured to perform adjustment determination including determination of whether or not at least one of first information regarding a motion amount between adjacent frame images of an object image in the captured image or second information regarding a blurring amount of an edge of the object image in the captured image satisfies an adjustment condition, and perform the adjustment processing by adjusting an adjustment level representing a degree of strength of the adjustment processing by a magnitude of a value according to a determination result of the adjustment determination; and a monitor configured to display the frame image subjected to the image processing on the screen, wherein:

the adjustment unit adjusts a luminance level of an image obtained by the image sensor by using a dimming amount set to decrease a value from a currently set value in a case where the luminance level of a current frame image is greater than a target luminance level and increase a value from the currently set value in a case where the luminance level of the current frame image is less than the target luminance level, the dimming amount being a parameter for performing adjustment such that the luminance level of the current frame image acquired by the image capturing of the image sensor is the target luminance level, the adjustment unit includes a first reference table and a second reference table which determine a level of the light intensity, a time length of the exposure time, and a gain level of the gain adjustment with respect to the dimming amount, the products obtained by multiplying each value of the level of the light intensity, the time length of the exposure time, and the gain level of the gain adjustment with respect to the value of the dimming amount coincide with each other between the first reference table and the second reference table over an entire range of possible values of the dimming amount, and a correspondence relationship of the level of the light intensity with respect to the value of the dimming amount and a correspondence relationship of the time length of the exposure time with respect to the value of the dimming amount are different from each other between the first reference table and the second reference table, and by using a first set value of each of the level of the light intensity, the time length of the exposure time, and the gain level, which are determined from the first reference table according to the value of the dimming amount, and a second set value of each of the level of the light intensity, the time length of the exposure time, and the gain level, which are determined from the second reference table according to the value of the dimming amount, the adjustment unit is configured to determine an adjustment value of the level of the light intensity, the adjustment value of the time length of the exposure time, and the adjustment value of the gain level which are used in the adjustment processing by performing interpolation according to the adjustment level between the first set value and the second set value corresponding to the first set value.

12. The endoscope system according to claim 11, wherein the adjustment unit further determines whether or not third information regarding the dimming amount satisfies the adjustment condition as the adjustment determination, and the determination result of the adjustment determination includes a determination result for the third information.

13. The endoscope system according to claim 12, wherein the third information regarding the dimming amount includes at least one of a change amount in the current dimming amount with respect to the immediately previous dimming amount or a maintaining time for maintaining the dimming amount at a value lower than a predetermined value.

14. An endoscope system that displays an image obtained by capturing a biological tissue in a body cavity on a screen, the endoscope system comprising:

a light source device configured to generate illumination light illuminating the biological tissue;

an electronic endoscope including an image sensor configured to capture the biological tissue as a moving image by a rolling shutter method;

a processor including an image processing unit configured to perform image processing on a frame image obtained by image capturing of the image sensor, an index calculation unit configured to calculate an artifact occurrence index indicating a degree that an artifact occurs along a line corresponding to a scanning line of the image sensor in the frame image due to the rolling shutter method, and an adjustment unit that is a part performing adjustment processing of adjusting luminance of the frame image by combining adjustment of an exposure time of the image sensor with at least one of adjustment of light intensity of the illumination light or gain adjustment for determining a signal level of an imaging signal of the frame image obtained from the image sensor, the adjustment unit being configured to perform the adjustment processing by adjusting an adjustment level representing a degree of strength of the adjustment processing by a magnitude of a value according to a determination result of whether or not a magnitude of the artifact occurrence index satisfies an adjustment condition; and a monitor configured to display the frame image subjected to the image processing on the screen, wherein:

the adjustment unit adjusts a luminance level of an image obtained by the image sensor by using a dimming amount set to decrease a value from a currently set value in a case where the luminance level of a current frame image is greater than a target luminance level and increase a value from the currently set value in a case where the luminance level of the current frame image is less than the target luminance level, the dimming amount being a parameter for performing adjustment such that the luminance level of the current frame image acquired by the image capturing of the image sensor is the target luminance level, the adjustment unit includes a first reference table and a second reference table which determine a level of the light intensity, a time length of the exposure time, and a gain level of the gain adjustment with respect to the dimming amount, the products obtained by multiplying each value of the level of the light intensity, the time length of the exposure time, and the gain level of the gain adjustment with respect to the value of the dimming amount coincide with each other between the first reference table and the second reference table over an entire range of possible values of the dimming amount, and a correspondence relationship of the level of the light intensity with respect to the value of the dimming amount and a correspondence relationship of the time length of the exposure time with respect to the value of the dimming amount are different from each other between the first reference table and the second reference table, and by using a first set value of each of the level of the light intensity, the time length of the exposure time, and the gain level, which are determined from the first reference table according to the value of the dimming amount, and a second set value of each of the level of the light intensity, the time length of the exposure time, and the gain level, which are determined from the second reference table according to the value of the dimming amount, the adjustment unit is configured to determine an adjustment value of the level of the light intensity, the adjustment value of the time length of the exposure time, and the adjustment value of the gain level which are used in the adjustment processing by performing interpolation according to the adjustment level between the first set value and the second set value corresponding to the first set value.

15. The endoscope system according to claim 14, wherein in both of the first reference table and the second reference table, the product obtained by multiplying each value of the level of the light intensity, the time length of the exposure time, and the gain level at a maximum value of the dimming amount is greater than the product obtained by multiplying each value of the level of the light intensity, the time length of the exposure time, and the gain level at a minimum value of the dimming amount, the time length of the exposure time of the second reference table is not shorter than the time length of the corresponding exposure time of the first reference table over the entire range of the possible values of the dimming amount, and the product of the value of the level of the light intensity and the value of the gain level in the second reference table is not greater than the product of the value of the level of the corresponding light intensity and the value of the corresponding gain level in the first reference table over the entire range of the possible values of the dimming amount.

16. The endoscope system according to claim 14, wherein the first reference table and the second reference table have a range of the dimming amount in which with respect to the value of the dimming amount, the time length of the exposure time of the second reference table is longer than the time length of the exposure time of the first reference table and the level of the light intensity of the second reference table is smaller than the level of the light intensity of the first reference table.

17. The endoscope system according to claim 14, wherein a value of the adjustment level is higher as a degree of the adjustment processing is stronger, and the adjustment value approaches the second set value as the value of the adjustment level is higher.

* * * * *